US006967019B2

(12) United States Patent
German

(10) Patent No.: US 6,967,019 B2
(45) Date of Patent: *Nov. 22, 2005

(54) PRODUCTION OF PANCREATIC ISLET CELLS AND DELIVERY OF INSULIN

(75) Inventor: Michael S. German, Daly City, CA (US)

(73) Assignee: The Regents of the University of California, Oakland, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 09/817,360

(22) Filed: Mar. 20, 2001

(65) Prior Publication Data

US 2002/0015696 A1 Feb. 7, 2002

Related U.S. Application Data

(63) Continuation-in-part of application No. 09/535,145, filed on Mar. 24, 2000, now Pat. No. 6,703,220.
(60) Provisional application No. 60/128,180, filed on Apr. 6, 1999.

(51) Int. Cl.[7] .......................... A01N 63/00; A61K 48/00
(52) U.S. Cl. .................... 424/93.21; 435/325; 435/366; 435/372; 435/375; 435/377; 435/455; 435/370
(58) Field of Search .................................. 435/325, 455, 435/366, 370, 372, 375, 377, 456, 351, 350, 353, 354, 320.1; 514/44; 424/93.21, 97.21

(56) References Cited

U.S. PATENT DOCUMENTS

| 5,741,673 A | * | 4/1998 | Montminy et al. ........ 435/69.1 |
| 5,795,723 A | | 8/1998 | Tapscott et al. |
| 5,830,730 A | | 11/1998 | German et al. |
| 5,858,973 A | * | 1/1999 | Habener et al. .............. 514/12 |
| 6,127,598 A | | 10/2000 | German et al. |
| 6,566,496 B1 | * | 5/2003 | Anderson et al. ........... 530/350 |
| 6,703,220 B1 | * | 3/2004 | German et al. ............ 435/69.1 |
| 2002/0015696 A1 | | 2/2002 | German |
| 2003/0082810 A1 | | 5/2003 | Serup |

FOREIGN PATENT DOCUMENTS

| WO | WO 96/34093 | 10/1996 |
| WO | WO 98/13491 | 4/1998 |
| WO | WO 00/09676 | 2/2000 |
| WO | WO 00/59936 | 10/2000 |
| WO | WO 01/01130 | 1/2001 |

OTHER PUBLICATIONS

Palgi et al., Molecular and Cellular Endocrinology 165:41–49, 2000.*
Gu et al., Development 129:2447–2457, 2002.*
Zhang et al. Diabetes vol. 50, S10–S14, 2001.*
Smith et al. JBC 2003, pp. 1–25, as manuscript M302229200.*
Street et al., Current Topics in Developmental Biology, vol. 58: 111–136, 2003.*
Soria et al., Diabetologia, 44:407–415, 2001.*
Soria, Differentiation, 2001, 68: 205–219.*
Huang, H–P. et al., Regulation of the Pancreatic Islet–Specific Gene BETA2 (neuroD) by Neurogenein 3. Molecular and Cellular Biology. May 200, vol. 20, 3292–3307 (May 2000).
Malecki, M.T. et al., Mutations in Nerod1 are Associated with the Development of Type 2 Diabetes Mellitus, Nature Genetics. Nov. 1999, vol. 23, pp. 323–328 (Nov. 1999).
Schmied, B.M. et al, Differentiation of Islet Cells in Long–Term Culture. Pancreas. vol. 20, No. 4, pp. 337–347 (2000).
Xu, W, et al., Isolation and Charachterization of the Mouse Beta2/neuroD Gene Promoter. Biochemical and Biophysical Research Communications. 1998, vol. 247, pp. 814–818. (1998).
Gradwohl, et al. "Neurogenin3 is required for the development of the four endocrine cell lineages of the pancreas", Proc. Natl. Acad. Sci. USA., (2000) vol. 97(4): 1607–1611.
Huang, et al. "Transcription factors involved in pancreatic islet development", J. Biomedical Sci., (2000) vol. 7(1): 27–34.
Jensen, et al. "Independent development of pancreatic alpha and beta cells from neurogenin3—expressing precursors: A role for the Notch pathway in repression of premature differentiation", Diabetes, (2000) vol. 49(2): 163–176.
Ravassard, et al. "Relax, a novel rat bHLH transcriptional regulator transiently expressed in the ventricular proliferating zone of the developing central nervous system", Canadian J. Chem., (1997) vol. 48(2): 146–158.
Ravassard, et al. "Homo sapiens gene for neurogenin3", Database EMBL Online, (1999) Database accession No. AJ33776.
Rudinger, "Characteristics of the amino acids as components of a peptide hormone sequence" in Peptide Hormones (ed. J.A. Parson), (1976) pp. 1–7, University Park Press, Baltimore.
Sommer, et al., "Neurogenins, a novel family of atonal–related bHLH transcription factors, are putative mammalian neuronal determination genes that reveal progenitor cell heterogeneity in the developing CNS and PNS," Molecular and Cellular Neuroscience, (1996) vol. 8: 221–241.

(Continued)

Primary Examiner—Scott D. Priebe
Assistant Examiner—Brian Whiteman
(74) Attorney, Agent, or Firm—James S. Keddie; Carol L. Francis; Bozicevic, Field & Francis LLP

(57) ABSTRACT

The present invention relates to the production of islet cells and insulin in a subject by providing for expression of an islet transcription factors in the pancreas of the subject, by for example, introduction of nucleic acid encoding the transcription factor neurogenin3 or a factor that induces neuorgenin3 expression. The present invention also relates to methods for using a islet transcription factor gene and the islet transcription factor polypeptide to alter cellular differentiation in culture or in vivo to produce new β-cells to treat patients with diabetes mellitus.

21 Claims, 20 Drawing Sheets

OTHER PUBLICATIONS

GenBank Accession No. U76208, deposited Feb. 5, 1997.
GenBank Accession No. Y09167, deposited Nov. 14, 1997.
GenBank Accession No. Y10619, deposited May 6, 1997.
GenBank Accession No. AJ133776.1, deposited Jun. 19, 1999.
GenBank Accession No. NM_020999, deposited Nov. 29, 2000.
Furuta et al. (Aug. 1998), "Beta–Cell Transcription Factors and Diabetes." *Diabetes*, vol. 47:1356–1358.
Goldfine et al. (Dec. 1997), "The Endocrine Secretion of Human Insulin and Growth Hormone by Exocrine Glands of the Gastrointestinal Tract." *Nature Biotechnology*, vol. 15:1378–1382.
Horikawa et al. (Nov. 2000), "Beta–Cell Transcription Factors and Diabetes." *Diabetes*, vol. 49:1955–1957.
Iannotti et al. (1997), "Identification of a Human LMX1 (LMX1.1)–Related Gene, LMX1.2:Tissue Specific Expression and Linkage Mapping Chromosome 9." *Genomics*, vol. 43:520–524.
Inoue et al. (1997), "Isolation, Characterization, and Chromosomal Mapping of the Human Nkx6.1 Gene (NKX6A), a New Pancreatic Islet Homeobox Gene." *Genomics*, vol. 40:367–370.
Muramura et al. (May 12, 2000), "Beta–Cell Differentiation Factor Nkx6.1 Contains Distinct DNA Binding Interference and Transcriptional Repression Domains." *The Journal of Biochemistry*, vol. 275(19):14743–14751.
Odagiri et al. (Jan. 26, 1996), "Function of the Human Insulin Promoter in Primary Cultured Islet Cells." *The Journal of Biochemistry*, vol. 271(4):1909–1915.
Ogata et al. (Mar. 2001), "Mutations in the Coding Region of Neurogenin 3 Gene (NEUROG3) are no Common Cause of Maturity–Onset Diabetes in Japanese Subject." *Diabetes*, vol. 50(3):694–696.
Rudnick et al. (Dec. 1994), "Pancreatic Beta Cells Express a Diverse Set of Homeobox Genes." *Proc. Natl. Acad. Sci. USA*, vol. 91:12203–12207.

Sander et al. (Sep. 1998), "A Novel Glucose–Responsive Element in the Human Insulin Gene Function as Uniquely in Primary Islets." *Proc. Natl. Acad. Sci. USA*, vol. 95:11572–11577.
Sander et al. (1997), "The beta Cell Transcription Factors and Development of the Pancreas." *J. Mol. Med.*, vol. 75:327–340.
Sander et al. (1997), "Genetic Analysis Reveals that PAX6 is Required for Normal Transcription of Pancreatic Hormone Genes and Islet Development." *Genes and Development*, vol. 11:1662–1673.
Sander et al. (2000), "Homeobox Gene Nkx6.1 Lies Downstream of Nkx.2.2 in the Major Pathway of Beta–Cell Formation in the Pancreas." *Development*, vol. 127:5533–5540.
Schwizgebel et al. (2000), "Expression of Neurogenenin3 Reveals an Islet Cell Precursor Population in the Pancreas." *Development*, vol. 127:3533–3542.
Sussel et al. (1998), "Mice Lacking the Homeodomain Transcription Factor Kkx2.2 Have Diabetes due to Arrested Differentiation of Pancreatic Beta Cells." *Development*, vol. 125:2213–2221.
Wang et al. (Apr. 1997), "Regulation of Insulin preRNA Splicing by Glucose." *Proc. Natl. Acad. Sci. USA.*, vol. 94:4360–4365.
Watada et al. (2000), "Transcriptional and Translational Regulation of Beta–Cell Differentiation Factor Nkx6.1." *The Journal of Biological Chemistry*, vol. 275(44):34224–34230.
Schwitzgebel et al., Expression of Neurogenin3 Reveals an Islet Cell Precursor Population in the Pancreas, Development, 2000, 127: 3533–3542.
Vetere et al., Neurogenin3 Triggers β–Cell Differntiation of Retinoic Acid–Derived Endoderm Cells, Biochem. J., 2003, 371: 831–841.

* cited by examiner

FIG. 6A  WT 
FIG. 6B  pdx1-ngn3
FIG. 6C  pdx1-neuroD1 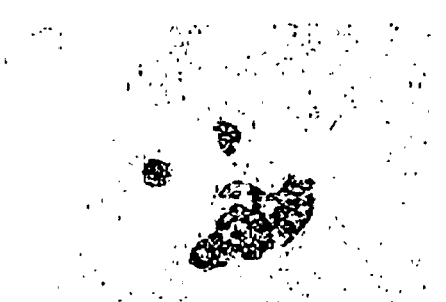

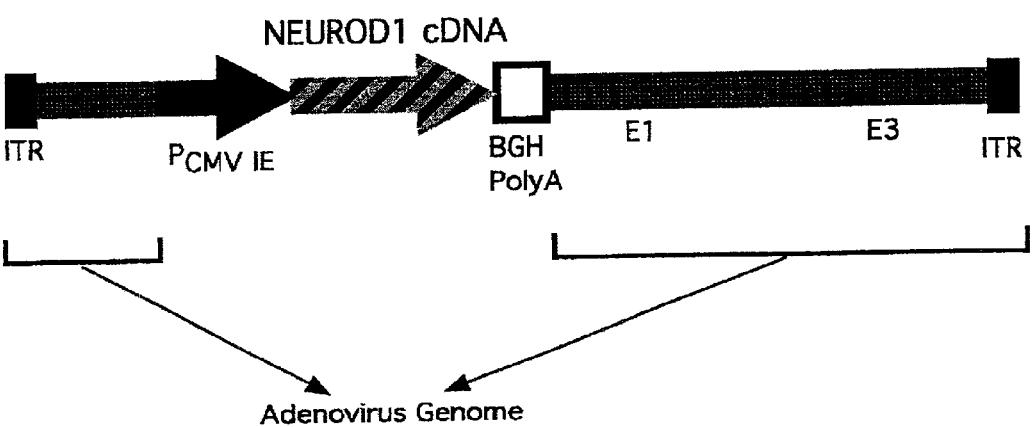
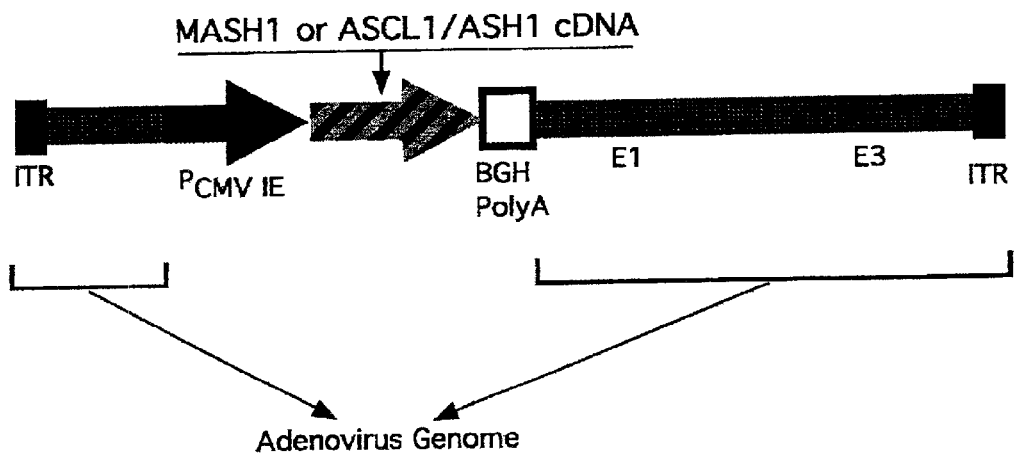
FIG. 8

SEQ ID NO:19

5.7 kb promoter

5.7 kb promoter glucagon/βGal 2.6 kb promoter insulin/glucagon/βGal neurogenin3/βGal neurogenin3/βGal

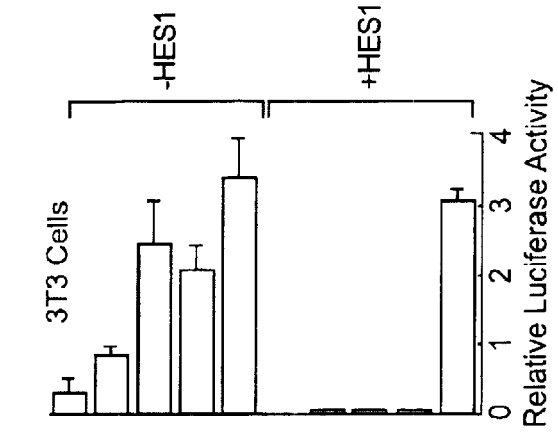
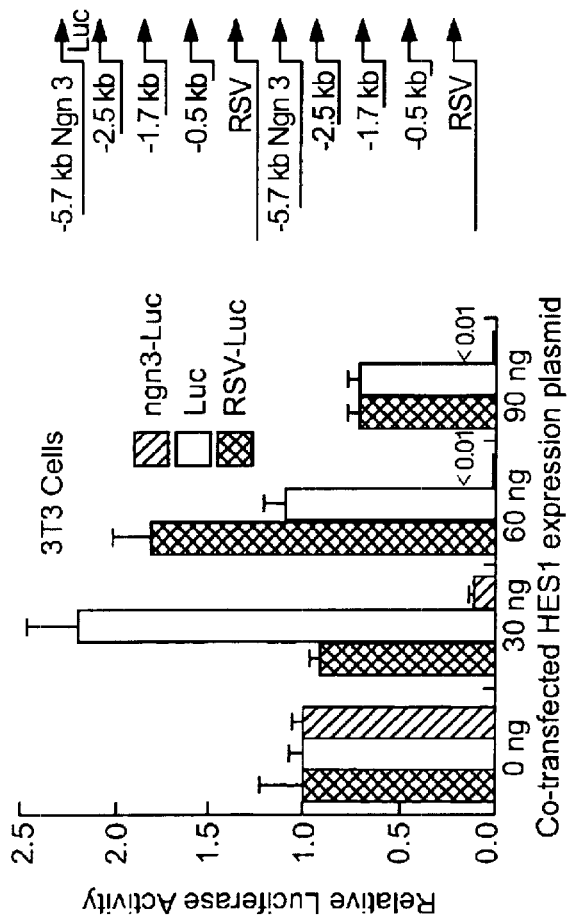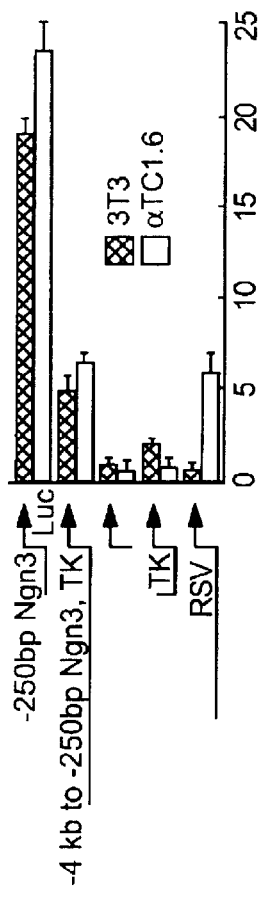
FIG. 18A
FIG. 18B
FIG. 18C

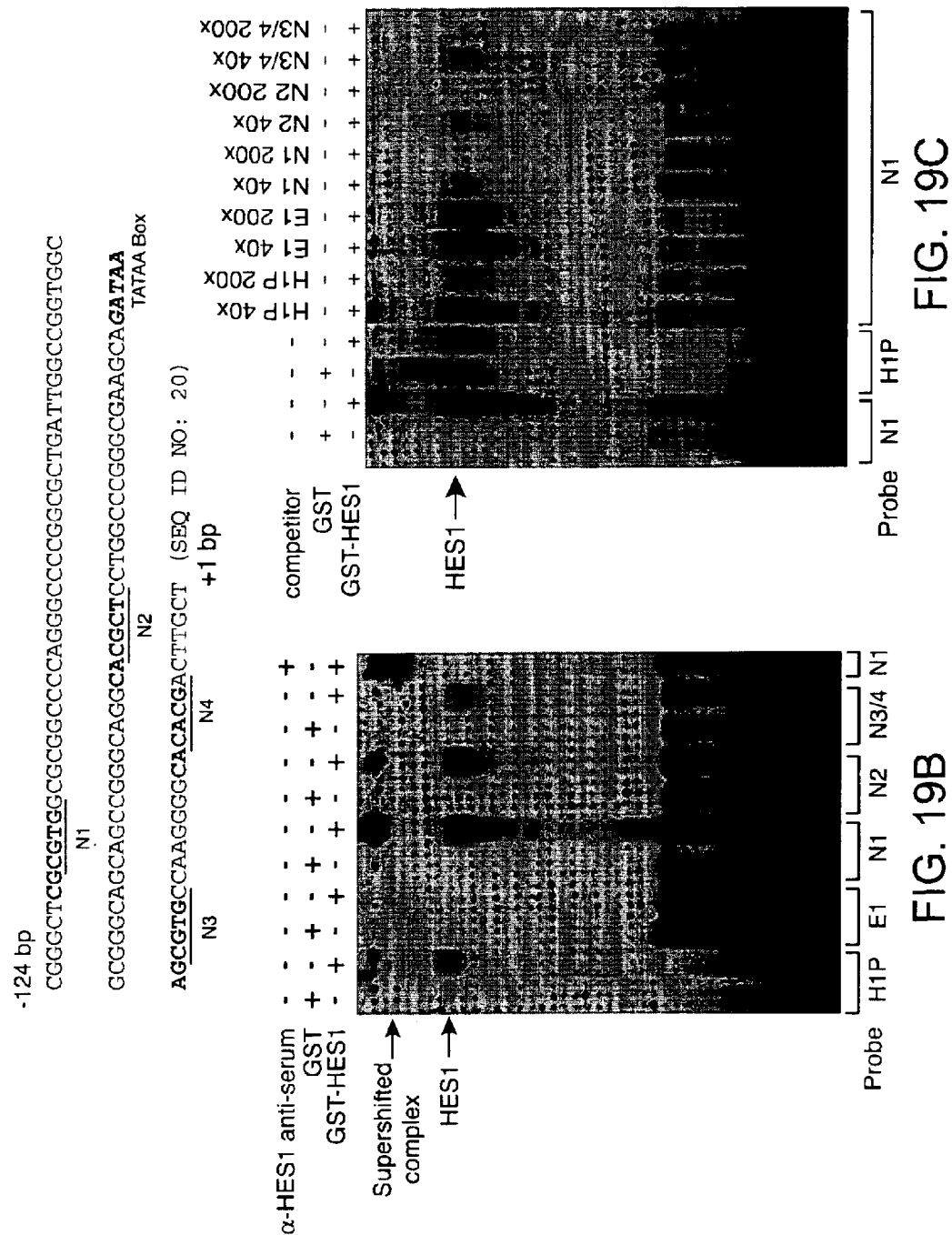

SEQUENCE LISTING

```
<160> NUMBER OF SEQ ID NOS: 20

<210> SEQ ID NO 1
<211> LENGTH: 5340
<212> TYPE: DNA
<213> ORGANISM: Homo Sapiens

<400> SEQUENCE: 1
```

```
ggatccctcg tggccagggt tcccttcaag gtgcttagcc aggtcaggag gccctagaga      60
agcatggttt ggattttctt tcccagacca aaaaagctcc aagttggttc tctcccagtt     120
tctaacttgc agttaaataa atcaggcaag gctggcctat gaggcagaca agtgtgaaga     180
aggagaagga ggaggagaag gagaaggaga agaagaaga aggaggagaa gaagaagaag     240
aagaagaaga agaagaggag gaggaggagg aggaggagga agcagcagca gcagcagcag     300
cttgaatgga cagtggttcc ccttgcctag aaaatgggac cattatttct tttctaatct     360 gaccccccaga ctcaggactt cctctatttt ctgcattttg gggtctcttg ttttgccttg     420
aaaaaaaatg ttttctccca aatcaaggag cagtagctgg tgcaagggaa aatctagggc     480
taggagtctt aagatatgac ttctatgtgg ttctgataga acttgctggg tgaccttgag     540
agagtcactc ccctctctg ggccttgatt ttttcatctt taaagaaggc ctcaaattcc      600
cattcttatg agaagaagac aagctcctag tgagtggtga cctaagggag cagctgcagc     660
aaaatgctaa cctgacagtc ccagatggtc cctttattgg ttctgaccct ggtctcaggc     720
ttcatttccc cacagcaagg gaaggagcct gctcacagag caccagctaa gatcagcagg     780
accgcgccac acccccgccc agtcctagag cccccctctc gctggttcct gagcatacca     840
ccctcttcct tggaggaaaa tttgccccca agcagcctag gcggtaagag gctatcacta     900
gggcagactc acagacctac ctcatcccct cacccacccc tacagtctcg aagtcgggtc     960
ctgtcccctc ctgcagtttc cgggagactc aggatatctg gacctgctag aaagagaagc    1020
cttcctcgcc taaggagact taaaccggga tacttaaacc tcccgcctcg gcgtcttcct    1080
ccaggcacga ccgggtcaag agagagaagc ggaagctgca acccctcact ctgagtgacc    1140
ggaagcagaa gaccacggga tgtcccaggc ggggacaaga ggaggggctg gggaagaaag    1200
gagggatgat gagttcagag tccctttgga aaggtttcca gagagcgcta ccagggacaa    1260
cccaaggggc tggggaagtc cctgccttgt gctctctgtg cgatgcccga gtgatgcaga    1320 ggcaggggc tggagcaggt gactgctggc agctgctgtc tgtctgtgat tggaccggag    1380
gactaagggg agaaaaagtt tatcagcttc tcccagtgcc tgcacgctgt ggtagttcaa    1440
aagacacgag ggggagggc acagcagctc tgcttcccag cgccttggga gactgaagtg    1500
aaaggaacgc ttgagcccag gagttcgaga ccatcctggg caacaaagca agaccgcccc    1560
tcaccccata caaaataaaa atacaaataa attagccggg cacagtggcg catgcctgta    1620
gtctcagcta ctgggaaggc tgaagtggga ggatagcttg agcccaggag atcaaggctg    1680
cagtgagctg tgattgcacc actgcagtcc agcctgggcg acagaaggag accgtttttt    1740
ggttttgttt gttcgtttaa aaaaaaaaag aagcaagagc tcactgtgaa ctcctggttc    1800
cttcctcccc tcctcacact tcccagaact cttcctgtca cggttcctgg ccagaacgct    1860
gggatactat ctacaagctg tagtaggctt gtagtaatgg aatgtccgct tgaggggtcc    1920
ccgcacagcc aaccccggcc tctggagtgg gatctatggg ggtgggggttc taagcgcctc    1980 tggggagtgt gaggtagcat ctcagggtgt ggcagaggct cggacacccc caaaaggtct    2040
gtgaatggaa gggacatagg caggatctct ctcagtgatg tccctgtct tccaggatga    2100 agagaggcag tgaaacacca ggagagcagg gcgtccttta gaattcctgg acccttctcc    2160
aggctgctag tcaggacaat gagctcgtgg ttgtcttttgc cactatcttc ctgtgcgatt    2220
tcagacaagc cacctccctc actaagccta aatttcccca tgtgtaacgt gcaggcattg    2280
taccctagag gcatcaaagt ccccctccagg acagatgcta aggaaagata ggctaggagc    2340
```

```
aaagccgtct gaggtggcct gaccagagcc acacgaggct cttctcactg ggcgaggctc    2400
tttgaggaac cgagagttgc tgggacccag cccgccctcg agagagcaaa cagagcggcg    2460
ctcccctccc ccgaccccgg cccttttgtcc ggaatccagc tgtgctgcgg gggaggagcg    2520
ggctcgcgtg gcgcggcccc agggcccggg cgctgattgg ccggtggcgc gggcagcagc    2580
cgggcaggca cgctcctggc ccgggcgaag cagataaagc gtgccaaggg gcacacgact    2640
tgctgctcag gaaatccctg cggtctcacc gccgcgcctc gagagagagc gtgacagagg    2700
cctcggaccc cattctctct tcttttctcc tttgggctg gggcaactcc caggcggggg    2760
cgcctgcagc tcagctgaac ttggcgacca gaagcccgct gagctcccca cggccctcgc    2820
tgctcatcgc tctctattct tttgcgccgg tagaaaggta atatttggag gcctccgagg    2880
gacgggcagg ggaaagaggg atcctctgac ccagcggggg ctgggaggat ggctgttttt    2940
gttttttccc acctagcctc ggaatcgcgg actgcgccgt gacggactca aacttaccct    3000
tccctctgac cccgccgtag gatgacgcct caaccctcgg gtgcgcccac tgtccaagtg    3060
acccgtgaga cggagcggtc cttccccaga gcctcggaag acgaagtgac ctgccccacg    3120
tccgccccgc ccagccccac tcgcacacgg gggaactgcg cagaggcgga agagggaggc    3180
tgccgagggg ccccgaggaa gctccgggca cggcgcgggg gacgcagccg gcctaagagc    3240
gagttggcac tgagcaagca gcgacggagt cggcgaaaga aggccaacga ccgcgagcgc    3300
aatcgaatgc acaacctcaa ctcggcactg gacgccctgc gcggtgtcct gcccaccttc    3360
ccagacgacg cgaagctcac caagatcgag acgctgcgct tcgcccacaa ctacatctgg    3420
gcgctgactc aaacgctgcg catagcggac cacagcttgt acgcgctgga gccgccggcg    3480
ccgcactgcg gggagctggg cagcccaggc ggttccccg gggactgggg gtccctctac    3540
tccccagtct cccaggctgg cagcctgagt cccgccgcgt cgctggagga gcgacccggg    3600
ctgctggggg ccacctcttc cgcctgcttg agcccaggca gtctggcttt ctcagatttt    3660
ctgtgaaagg acctgtctgt cgctgggctg tgggtgctaa gggtaaggga gagggaggga    3720
gccgggagcc gtagagggtg gccgacggcg gcggcccctca aaagcacttg ttccttctgc    3780
ttctccctgg ctgacccctg gccggcccag gctccacggg ggcggcaggc tgggttcatt    3840 ccccggcccct ccgagccgcg ccaacgcacg caacccttgc tgctgcccgc gcgaagtggg    3900
cattgcaaag tgcgctcatt ttaggcctcc tctctgccac cacccccataa tctcattcaa    3960 agaatactag aatggtagca ctacccggcc ggagccgccc accgtcttgg gtcgccctac    4020
cctcactcaa gtctgtctgc ctctcagtct cttaccaccc ctcctccaat gtgattcaat    4080
ccaatgtttg gtctctcagc gcttactccc cttgccttgc tccaaagacg ctgccgatct    4140
gctctactcc caatcaggtc cgggatttca gggcgcctca ctctgcctta aagccacgaa    4200
ggcgaccctc tgccttctcc tcgtgcactt ttcggagcca ttgccctccc ggggcggaag    4260
accaggctgt gaactgggaa agcgctagcc cggccaggga gcatctcccc agcctccctg    4320
cgaactgcgc ctgaaacgtg agctgcgctg caggtgcctg gagcaccgcg catctttttt    4380
ttttaaatct gtttgtaaat tatatgatgc cttttgaaat caattttggt acagtaaaat    4440
tatatggccc ctcccctgtt ttacacattt gtatttatta atgagatttc acagcaggga    4500
aaagcctata ttttggatat tagattattt agggattgct ggatgacatt taagccaata    4560
aaaaaaaatg gaccttcaag aagccttggc aagatgactc cattgtgtgt tggggagagg    4620
agggccacag tcactacagc tgaggaagag cacttctgtc caaagagagg gatgacactc    4680
tttctggagg tctgggctag agccagggca gattgggttt ggagagctgg aagtcttcta    4740
```

-continued

```
agtaattatt ggtccagctc ccttttttct atataggggca atgactcctc ttatttcaaa    4800
gagtggttta gaagaaagac aagcctccaa ctaggacaac tgactctcac ttgctggccc    4860
tttccccaac tccaccagcc tagctttaga gcaactgttg gttgcacttg gggaagggat    4920
acagtaataa ttcaattgca gagtcagagt cctcggaaac acggctgggc tgggcatcct    4980
aggaattttc ccaaggtgct tagaggccta gcaaatcccc tgagcatatt ttactcccca    5040
ggcactgagg tggctgtgtc gtgaactcct tgaactgagc agccaggagc aaagaaggtg    5100
gagcgtctgg ctggaatatc cagcaacgcc ccctccctca tcacctggca gccttgattg    5160
aaaacttatt aagaaactgt tcaaggtttc cagccacacc atgtctctta ctggcaaggt    5220
ggaataggac tggtgcagca tgagcactga aatctgtccc aggagtgcca gtagagcacc    5280
actacatgac ttcagggacc cctaggacct cagagaatat ggtctaagct gtaaggatcc    5340
```

<210> SEQ ID NO 2
<211> LENGTH: 214
<212> TYPE: PRT
<213> ORGANISM: Homo Sapiens

<400> SEQUENCE: 2

```
Met Thr Pro Gln Pro Ser Gly Ala Pro Thr Val Gln Val Thr Arg Glu
 1               5                   10                  15

Thr Glu Arg Ser Phe Pro Arg Ala Ser Glu Asp Glu Val Thr Cys Pro
                20                  25                  30

Thr Ser Ala Pro Pro Ser Pro Thr Arg Thr Arg Gly Asn Cys Ala Glu
            35                  40                  45

Ala Glu Glu Gly Gly Cys Arg Gly Ala Pro Arg Lys Leu Arg Ala Arg
        50                  55                  60

Arg Gly Gly Arg Ser Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Leu Tyr Ala Leu Glu Pro Pro Ala Pro His Cys Gly Glu Leu Gly
145                 150                 155                 160

Ser Pro Gly Gly Ser Pro Gly Asp Trp Gly Ser Leu Tyr Ser Pro Val
                165                 170                 175

Ser Gln Ala Gly Ser Leu Ser Pro Ala Ala Ser Leu Glu Glu Arg Pro
            180                 185                 190

Gly Leu Leu Gly Ala Thr Ser Ser Ala Cys Leu Ser Pro Gly Ser Leu
        195                 200                 205

Ala Phe Ser Asp Phe Leu
    210
```

<210> SEQ ID NO 3
<211> LENGTH: 1861
<212> TYPE: DNA
<213> ORGANISM: Mus musculus

<400> SEQUENCE: 3

-continued

```
ggatcccaag gtgatattga acctggccaa gcaatagttt ctgagtgaaa aggacttgag      60
cagggaccgt ctctggtcac tctgtcctct ttcccaggat ggagtcagtc tgtgaaacat     120
ggttgcacac acatttcctg acccaaccca tagtggcgga gagctggata gcactttgaa     180
ctaatgggcg ctcctcccag ctgccagcca agaagacact tgactccttg atcgctggtt     240
catttagaca agccgtttcc ctctctgagc caaaagaccc catgtgtaat actcaaagaa     300
gaggccttcc ttatatatat ataggcaccc ccaaacctcc ttcatgctac caagaaaggg     360
tctggacaca tgccaaaaag aaagaggaaa aggcaaagct ctccccagcg gccggacggg     420
actcttctgg ctgggcgagg ctctttgagg aaccgagagt tgctgggact gagcccgcga     480
cgggggaggc gtggagtggg ggaacaaaca gagtgctgct cccctccccc gaccccctgcc    540
ctttgtccgg aatccagctg tgctctgcgg gtgggggttg tgggggggagg agcgggctcg   600
cgtggcgcag ccctggggcc ccctccgctg attggcccgt ggtgcaggca gcagcccggc    660
aggcacgctc ctggccgggg gcagagcaga taaagcgtgc caggggacac acgacttgca    720
tgcagctcag aaatccctct gggtctcatc actgcagcag tggtcgagta cctcctcgga    780
gcttttctac gacttccaga cgcaatttac tccaggcgag ggcgcctgca gtttagcaga    840
acttcagagg gagcagagag gctcagctat ccactgctgc ttgacactga ccctatccac    900
tgctgcttgt cactgactga cctgctgctc tctattcttt tgagtcggga gaactaggta    960
acaattcgga aactccaaag ggtggatgag gggcgcgcgg ggtgtgtgtg ggggatactc   1020
tggtcccccg tgcagtgacc tctaagtcag aggctggcac acacacacct tccatttttt   1080
cccaaccgca ggatggcgcc tcatcccttg gatgcgctca ccatccaagt gtccccagag   1140
acacaacaac ctttccccgg agcctcggac cacgaagtgc tcagttccaa ttccacccca   1200
cctagcccca ctctcatacc tagggactgc tccgaagcag aagtgggtga ctgccgaggg   1260
acctcgagga agctccgcgc cgacgcggga gggcgcaaca ggcccaagag cgagttggca   1320
ctcagcaaac agcgaagaag ccggcgcaag aaggccaatg atcgggagcg caatcgcatg   1380
cacaacctca actcggcgct ggatgcgctg cgcggtgtcc tgcccacctt cccggatgac   1440
gccaaactta caaagatcga gaccctgcgc ttcgcccaca actacatctg ggcactgact   1500
cagacgctgc gcatagcgga ccacagcttc tatggcccgg agcccctgt gcctgtgga    1560
gagctgggga gccccggagg tggctccaac ggggactggg gctctatcta ctccccagtc   1620
tcccaagcgg gtaacctgag ccccacggcc tcattggagg aattccctgg cctgcaggtg   1680
cccagctccc catcctatct gctcccggga gcactggtgt tctcagactt cttgtgaaga   1740
gacctgtctg gctctgggtg gtgggtgcta gtggaaaggg aggggaccag agccgtctgg   1800
agtgggaggt agtggaggct ctcaagcatc tcgcctcttc tggctttcac tacttggatc   1860
c                                                                   1861
```

<210> SEQ ID NO 4
<211> LENGTH: 214
<212> TYPE: PRT
<213> ORGANISM: Mus musculus

<400> SEQUENCE: 4

```
Met Ala Pro His Pro Leu Asp Ala Leu Thr Ile Gln Val Ser Pro Glu
  1               5                  10                  15

Thr Gln Gln Pro Phe Pro Gly Ala Ser Asp His Glu Val Leu Ser Ser
             20                  25                  30

Asn Ser Thr Pro Pro Ser Pro Thr Leu Ile Pro Arg Asp Cys Ser Glu
```

-continued

```
                 35                  40                  45
Ala Glu Val Gly Asp Cys Arg Gly Thr Ser Arg Lys Leu Arg Ala Arg
    50                  55                  60

Arg Gly Gly Arg Asn Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Phe Tyr Gly Pro Glu Pro Pro Val Pro Cys Gly Glu Leu Gly Ser
145                 150                 155                 160

Pro Gly Gly Gly Ser Asn Gly Asp Trp Gly Ser Ile Tyr Ser Pro Val
                165                 170                 175

Ser Gln Ala Gly Asn Leu Ser Pro Thr Ala Ser Leu Glu Glu Phe Pro
            180                 185                 190

Gly Leu Gln Val Pro Ser Ser Pro Ser Tyr Leu Leu Pro Gly Ala Leu
        195                 200                 205

Val Phe Ser Asp Phe Leu
    210
```

```
<210> SEQ ID NO 5
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 5
tggagaactg tcaaagcgat ctg                                           23

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
cacatgccca gtttctattg gtc                                           23

<210> SEQ ID NO 7
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 7
atcctgcggt tgggaa                                                   16

<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer
```

-continued

```
<400> SEQUENCE: 8
tggaaggtgt gtgtgtgcca g                                      21

<210> SEQ ID NO 9
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 9
gatctagaga cttagaggtc actgc                                  25

<210> SEQ ID NO 10
<211> LENGTH: 30
<212> TYPE: DNA
<213> ORGANISM: Artificial Sequence
<220> FEATURE:
<223> OTHER INFORMATION: H3-1

<400> SEQUENCE: 10
gatctctcga gagagcaaac agcgcggcgg                             30

<210> SEQ ID NO 11
<211> LENGTH: 31
<212> TYPE: DNA
<213> ORGANISM: Artificial Sequence
<220> FEATURE:
<223> OTHER INFORMATION: H3-2

<400> SEQUENCE: 11
ttattattat tttagcaaac actggagaca g                           31

<210> SEQ ID NO 12
<211> LENGTH: 34
<212> TYPE: DNA
<213> ORGANISM: Artificial Sequence
<220> FEATURE:
<223> OTHER INFORMATION: H1

<400> SEQUENCE: 12
atctcttgta attatttatt aaacgaaatc tatt                        34

<210> SEQ ID NO 13
<211> LENGTH: 34
<212> TYPE: DNA
<213> ORGANISM: Artificial Sequence
<220> FEATURE:
<223> OTHER INFORMATION: H2

<400> SEQUENCE: 13
ttaaacgaaa tctatttatt attattttag caaa                        34

<210> SEQ ID NO 14
<211> LENGTH: 26
<212> TYPE: DNA
<213> ORGANISM: Artificial Sequence
<220> FEATURE:
<223> OTHER INFORMATION: H1P

<400> SEQUENCE: 14
gatctcgcca cgagccacaa ggattg                                 26

<210> SEQ ID NO 15
<211> LENGTH: 30
```

```
<210> SEQ ID NO 15
<211> LENGTH: 30
<212> TYPE: DNA
<213> ORGANISM: Artificial Sequence
<220> FEATURE:
<223> OTHER INFORMATION: E1

<400> SEQUENCE: 15
gatctaaatt tccccatgtg taacgtgcag                                      30

<210> SEQ ID NO 16
<211> LENGTH: 32
<212> TYPE: DNA
<213> ORGANISM: Artificial Sequence
<220> FEATURE:
<223> OTHER INFORMATION: N1

<400> SEQUENCE: 16
gatctggagc gggctcgcgt ggcgcggccc cg                                   32

<210> SEQ ID NO 17
<211> LENGTH: 31
<212> TYPE: DNA
<213> ORGANISM: Artificial Sequence
<220> FEATURE:
<223> OTHER INFORMATION: N2

<400> SEQUENCE: 17
gatctgccgg gcaggcacgc tcctggcccg g                                    31

<210> SEQ ID NO 18
<211> LENGTH: 31
<212> TYPE: DNA
<213> ORGANISM: Artificial Sequence
<220> FEATURE:
<223> OTHER INFORMATION: N3/4

<400> SEQUENCE: 18
gatctaaagc gtgccaaggg gcacacgact g                                    31

<210> SEQ ID NO 19
<211> LENGTH: 75
<212> TYPE: DNA
<213> ORGANISM: Homo sapiens

<400> SEQUENCE: 19
cttgtaatta tttattaaac gaaatctatt tattattatt ttagcaaaca ctggagacag     60
gtggggcttt ctttt                                                      75

<210> SEQ ID NO 20
<211> LENGTH: 126
<212> TYPE: DNA
<213> ORGANISM: Homo sapiens

<400> SEQUENCE: 20
cgggctcgcg tggcgcggcc ccagggcccc ggcgctgatt ggccggtggc gcgggcagca     60
gccgggcagg cacgctcctg gcccgggcga agcagataaa gcgtgccaag gggcacacga    120
cttgct                                                               126
```

PRODUCTION OF PANCREATIC ISLET CELLS AND DELIVERY OF INSULIN

CROSS-REFERENCE TO RELATED APPLICATION

This application is a continuation-in-part of U.S. application Ser. No. 09/535,145, filed Mar. 24, 2000 now U.S. Pat. No. 6,703,220 and also entitled to the benefit of U.S. Provisional Application Ser. No. 60/128,180, filed Apr. 6, 1999, the disclosures of which are incorporated herein by reference.

FIELD OF THE INVENTION

The invention relates generally to the field of delivery of insulin to a subject by production of islet cells, particularly insulin producing beta cells. More particularly, the invention relates to production of islet cells by modulation of expression of nucleotide sequences encoding transcription factors involved in growth and differentiation of pancreatic islet cells.

BACKGROUND OF THE INVENTION

Diabetes mellitus is the third leading cause of death in the U.S. and the leading cause of blindness, renal failure, and amputation. Diabetes is also a major cause of premature heart attacks and stroke and accounts for 15% of U.S. health care costs. Approximately 5% of Americans, and as many as 20% of those over the age of 65, have diabetes.

Diabetes results from the failure of the β-cells in the islets of Langerhans in the endocrine pancreas to produce adequate insulin to meet metabolic needs. Diabetes is categorized into two clinical forms: Type 1 diabetes (or insulin-dependent diabetes) and Type 2 diabetes (or non-insulin-dependent diabetes). Type 1 diabetes is caused by the loss of the insulin-producing β-cells. Type 2 diabetes is a more strongly genetic disease than Type 1 (Zonana & Rimoin, 1976 N. Engl. J. Med. 295:603), usually has its onset later in life, and accounts for approximately 90% of diabetes in the U.S. Affected individuals usually have both a decrease in the capacity of the pancreas to produce insulin and a defect in the ability to utilize the insulin (insulin resistance). Obesity causes insulin resistance, and approximately 80% of individuals with Type 2 diabetes are clinically obese (greater than 20% above ideal body weight). Unfortunately, about one-half of the people in the U.S. affected by Type 2 diabetes are unaware that they have the disease. Clinical symptoms associated with Type 2 diabetes may not become obvious until late in the disease, and the early signs are often misdiagnosed, causing a delay in treatment and increased complications. While the role of genetics in the etiology of type 2 diabetes is clear, the precise genes involved are largely unknown.

Insulin is made exclusively by the β-cells in the islets of Langerhans in the pancreas. During development, the islet cells, including the β-cells, develop from an undifferentiated precursor within the growing pancreatic bud. As the bud grows, the undifferentiated cells form into ducts, and it is these cells that function as precursors. Duct cells appear to retain the capacity to differentiate into islet cells throughout life, and in some circumstances when the pancreas is damaged, new islet cells can form from the duct cells. Unfortunately, islet cell regeneration does not appear to occur when the islet cells alone are damaged, such as in type 1 diabetes.

This developmental process is clinically relevant for several reasons. First, the formation of islet cells and especially β-cells is necessary in order to make insulin and control energy metabolism. If the process of β-cell development is in anyway impaired, it predisposes that individual to the later development of diabetes. Therefore genes involved in this process are candidate genes for neonatal diabetes, maturity onset diabetes of the young (MODY) or type 2 diabetes. The sequence of these genes could be used to identify individuals at risk for the development of diabetes, or to develop new pharmacological agents to prevent and treat diabetes.

Second, as discussed above, insulin production is impaired in individuals with diabetes. In type 1 diabetes the impairment is caused by the destruction of the β-cells, while in type 2 diabetes, insulin production is intact, but inadequate. Treatment of type 1 diabetes, as well as many cases of type 2 diabetes, may involve replacement of the β-cells. While replacement of β-cells may be accomplished in several ways, the development of new β-cells from precursor cells, either in culture or in vivo in the patient, would be the most physiologic. To do this, the molecules that control β-cell differentiation are needed.

For these reasons, the diabetes field has spent considerable effort in attempts to identify islet precursor cells, and to develop methods for differentiating beta-cells in vitro. To date this has been largely unsuccessful. The present invention addresses this problem.

Literature

A cloned fragment of mouse Ngn3 is described in Sommer et al. 1996 Mol. Cell. Neurosci. 8:221.

cDNA and amino acid sequences of murine Ngn3 and murine mammalian atonal homology 4B (MATH4B) are described at GenBank Accession Nos. U76208 and Y09167, respectively. The human ngn3 gene and mRNA are described at GenBank Accession Nos. AJ133776 and NM_020999, respectively.

cDNA and amino acid sequences of the rat relax transcriptional regulator are described at GenBank Accession No. Y10619.

SUMMARY OF THE INVENTION

The present invention relates to the production of islet cells and insulin in a subject by providing for expression of an islet transcription factors in the pancreas of the subject, by for example, introduction of nucleic acid encoding the transcription factor neurogenin3 or a factor that induces neuorgenin3 expression. The present invention also relates to methods for using a islet transcription factor gene and the islet transcription factor polypeptide to alter cellular differentiation in culture or in vivo to produce new β-cells to treat patients with diabetes mellitus.

A primary object of the invention is to provide for the production of islet cells in the pancreas of a subject.

Another object of the invention is to provide for the production of insulin in a subject by inducing the formation of functional β-cells.

Another object of the invention is to provide a method for using the islet transcription factor genes to alter cellular differentiation in culture or in vivo to produce new β-cells to treat patients with diabetes mellitus.

Another object of the invention is to provide for production of islet cells for ex vivo therapy, e.g. production of islet transcription factor expressing cells for transplantation into a subject.

These and other objects, advantages and features of the present invention will become apparent to those persons skilled in the art upon reading the details of the invention more fully set forth below.

The invention will now be described in further detail.

BRIEF DESCRIPTION OF THE DRAWINGS

The patent or application file contains at least one drawing executed in color. Copies of this patent application publication with color drawing(s) will be provided by the U.S. Patent and Trademark Office upon request and payment of the necessary fee.

FIG. 6 is a photograph showing the expression of the islet hormone in transgenic mice at embryonic day 12.5. Immunohistochemical staining is shown for glucagons in pancreases of a non-transgenic littermate (A) and transgenic fetuses expressing ngn3 (B) or neuroD1/BETA2 (C).

FIG. 8 is a map of the Adeno-X.NeuroD1 and Adeno-X.MASH1 viral construct, which contain the NeuroD1 and Mas1 sequences operably linked to the CMV promoter, respectively.

FIG. 11 A is a schematic representation of the promoter shows the relative positions of the transcription start site and the 5' ends of promoter fragments used in the Examples. Some potential sites for transcription factor binding are indicated, including a cluster of sites in the distal promoter. The TATAA box (actual sequence GATAA) is shown 30 bp upstream of the transcription start site. FIG. 11B The DNA sequence between positions −3728 and −3653 of the promoter corresponding to cluster 1 is shown. Again potential sites for transcription factor binding are indicated. Two sequences that could potentially function as binding sites for homeodomain proteins of the Hox and related classes are indicated by dashed lines.

In FIG. 13A, 5.7 kb of the human Ngn3 promoter was ligated upstream of the bacterial β-galactosidase gene and expressed in transgenic mice. The staining indicates β-galactosidase catalysis of the X-gal substrate in the labeled cells. FIGS. 13B and 13C show immunohistochemical staining (peroxidase detection) for glucagon (brown) with enzymatic detection (blue) of β-galactosidase expression is shown in the pancreas of E15.5 mouse embryos. β-galactosidase expression is driven by −5.7 kb or −2.6 kb of the human Ngn3 promoter as indicated. X-gal staining was performed for 16 hours at 37 (2.6 kb promoter) or at room temperature (5.7 kb promoter). Both sections show 10× magnification of comparable sections.

FIG. 14A shows a combination of florescent staining (for insulin (red) and glucagon (green)), and enzymatic detection of β-galactosidase expressed under the control of the 5.7 kb human neurogenin 3 promoter is shown in an E15.5 mouse pancreas. Co-expression of insulin and β-galactosidase in one cell is indicated by the arrow. FIG. 14B shows co-detection of Neurogenin3 (peroxidase staining) and β-galactosidase (enzymatic detection) is demonstrated in an E15.5 mouse pancreas. The arrows indicate cells that are expressing both neurogenin3 and β-galactosidase.

FIG. 15A shows the activity of the β-galactosidase transgene driven by the 5.7 kb human ngn3 promoter can be detected in scattered cells in the gut epithelium of a E15.5 mouse pancreas. FIG. 15B is a control, showing the lack of similar β-galactosidase expression in a wildtype litter mate. FIG. 15C shows detection of Ngn3 (peroxidase detection) in some cells also expressing β-galactosidase (filled arrows) and in some cells not expressing of β-galactosidase (white arrowhead) in an E15.5 transgenic mouse gut.

FIG. 16A shows an electromobility shift assay demonstrating the binding of transcription factor HNF3β to the H3-1 probe of the human ngn3 promoter. FIG. 16B shows an electromobility shift assay demonstrating that a proximal site and a distal site in the human Ngn3 promoter can compete equally for binding of HNF3β.

FIGS. 18A–18C are graphs showing that HES1 inhibits the neurogenin3 promoter. FIG. 18A shows results with NIH3T3 cells transfected with the reporter construct indicated, and co-transfected with the indicated amount of expression plasmid containing the HES1 cDNA ligated downstream of the CMV promoter (vector pBAT12). The luciferase activity is expressed relative to the activity in cells transfected with the reporter plasmid alone. FIG. 18B shows the relative activity of various fragments of the Ngn3 promoter and the Rous Sarcoma virus (RSV) promoter ligated upstream of luciferase in the presence or absence of co-transfection with 90 ng/million cells of the HES1 expression plasmid. FIG. 18C shows fold repression by cotransfected HES1 of luciferase activity from the indicated promoters in NIH 3T3 cells and TC1.6 cells. Fold repression is the inverse of relative luciferase activity. Transfections were performed in triplicate on at least 3 separate occasions. Errors are shown as +/- the standard error of the mean.

FIG. 19A is a schematic of the DNA sequence immediately upstream of the transcription start site (+1) of the human ngn3 gene is shown. Potential HES1 binding sites (N boxes) are indicated.

FIGS. 19B–19C are photographs of electromobility shift assays showing that HES1 binds to the human ngn3 promoter. FIG. 19B shows an electromobility shift assay demonstrating that bacterially produced HES1 can bind to the N boxes in the proximal promoter, as well as to a previously characterized site from the mouse HES1 promoter (H1P). Either GST-HES1 or GST protein was incubated with the indicated probes. The far right hand lane shows that the HES1 complex is supershifted by addition of HES1 antiserum. FIG. 19C shows an electromobility shift assay demonstrating the relative ability of HES1 binding sites to compete for binding of the GST-HES1 protein. All three ngn3 promoter sites bind with higher affinity than the previously described HES1 binding site from the HES1 promoter (H1P). In contrast, a 200 fold excess of oligonucleotide E1 (an unrelated E box sequence from the proximal promoter) has no effect on complex formation.

DETAILED DESCRIPTION OF THE INVENTION

Figure 1:
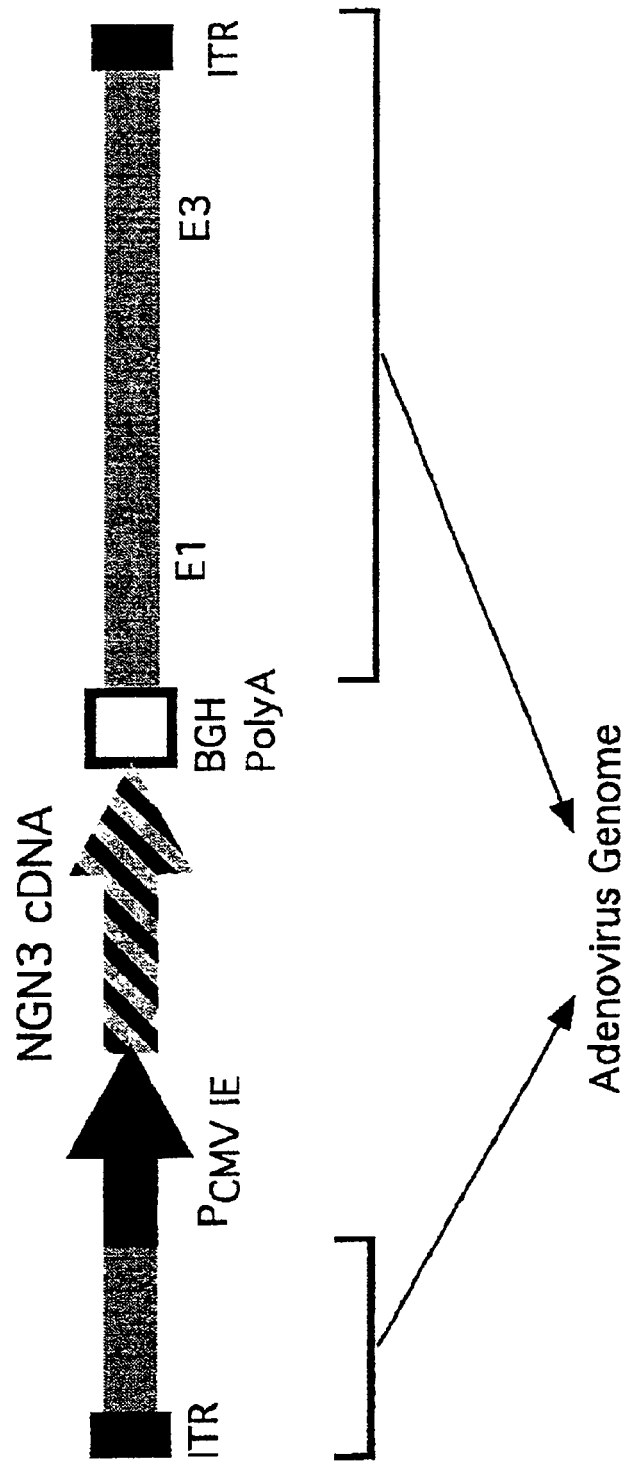
FIG. 1 is a map of the Adeno-X.NGN3 viral construct, which contains the murine neurogenin3 sequence operably linked to the CMV promoter.

Before the present compositions and methods for islet cell and insulin production are described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural referents unless the context clearly dictates otherwise. Thus, for example, reference to "an islet transcription factor" includes a plurality of such islet transcription factors and functional equivalents thereof, and reference to "the polynucleotide" includes reference to one or more polynucleotides and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

Definitions

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g. a Ngn3 polypeptide-encoding polynucleotide), "polynucleotide" is meant to encompass polynucleotides that encode a polypeptide that is functionally equivalent to the recited polypeptide, e.g., polynucleotides that are degenerate variants, or polynucleotides that encode biologically active variants or fragments of the recited polypeptide, including polynucleotides having substantial sequence similarity or sequence identity relative to the sequences provided herein. Similarly, "polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule, but instead is meant to also encompass biologically active variants or fragments, including polypeptides having substantial sequence similarity or sequence identify relative to the amino acid sequences provided herein.

As used herein, "polypeptide" refers to an amino acid sequence of a recombinant or nonrecombinant polypeptide having an amino acid sequence of i) a native polypeptide, ii) a biologically active fragment of an polypeptide, iii) biologically active polypeptide analogs of an polypeptide, or iv) a biologically active variant of an polypeptide. Polypeptides useful in the invention can be obtained from any species, e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human, from any source whether natural, synthetic, semi-synthetic or recombinant. For example, "Human Ngn3 polypeptide" refers to the amino acid sequences of isolated human Ngn3 polypeptide obtained from a human, and is meant to include all naturally-occurring allelic variants, and is not meant to limit the amino acid sequence to the complete, native amino acid sequence associated with the recited protein molecule.

As used herein, "antigenic amino acid sequence" means an amino acid sequence that, either alone or in association with a carrier molecule, can elicit an antibody response in a mammal.

A "variant" of a polypeptide is defined as an amino acid sequence that is altered by one or more amino acids. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, inserted or deleted without abolishing biological or immunological activity can be found using computer programs well known in the art, for example, DNAStar software.

By "nucleic acid of interest" is meant any nucleic acid (e.g., DNA) which encodes a protein or other molecule which is desirable for administration to a mammalian subject. In general, the nucleic acid is operatively linked to other sequences which are needed for its expression, such as a promoter.

A "deletion" is defined as a change in either amino acid or nucleotide sequence in which one or more amino acid or nucleotide residues, respectively, are absent as compared to an amino acid sequence or nucleotide sequence of a naturally occurring polypeptide of interest.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring polypeptide.

A "substitution" results from the replacement of one or more amino acids or nucleotides by different amino acids or nucleotides, respectively as compared to an amino acid sequence or nucleotide sequence of a naturally occurring polypeptide.

The term "biologically active", for example, refers to human Ngn3 polypeptide having structural, regulatory, or biochemical functions of a naturally occurring Ngn3 polypeptide. Likewise, "immunologically active" defines the capability of the natural, recombinant or synthetic human Ngn3 polypeptide, or any oligopeptide thereof, to induce a specific immune response in appropriate animals or cells and to bind with specific antibodies.

The term "derivative" as used herein refers to the chemical modification of a nucleic acid encoding a polypeptide or the encoded polypeptide. Illustrative of such modifications would be replacement of hydrogen by an alkyl, acyl, or amino group. A nucleic acid derivative would encode a polypeptide which retains essential biological characteristics of a natural polypeptide.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

By "transformation" or "transfection" is meant a permanent or transient genetic change, preferably a permanent genetic change, induced in a cell following incorporation of new nucleic acid (e.g., DNA or RNA exogenous to the cell). Genetic change can be accomplished either by incorporation of the new nucleic acid into the genome of the host cell, or by transient or stable maintenance of the new DNA as an episomal element.

By "transformed cell" is meant a cell into which (or into an ancestor of which) has been introduced, by means of recombinant DNA techniques, a DNA molecule encoding a protein of interest.

By "construct" is meant a recombinant nucleic acid, generally recombinant DNA, that has been generated for the purpose of the expression of a specific nucleotide sequence (s), or is to be used in the construction of other recombinant nucleotide sequences.

By "vector" is meant any compound, biological or chemical, which facilitates transformation of a target cell with a DNA of interest. Exemplary biological vectors include viruses, particularly attenuated and/or replication-deficient viruses. Exemplary chemical vectors include lipid complexes and naked DNA constructs.

By "naked DNA" or "naked nucleic acid" or DNA sequence and the like is meant a nucleic acid molecule that is not contained within a viral particle, bacterial cell or other encapsulating means that facilitates delivery of nucleic acid into the cytoplasm of the target cell. Naked nucleic acid can optionally be associated (e.g. formulated) with means for facilitating delivery of the nucleic acid to the site of the target cell (e.g., means that facilitate travel into the cell, protect the nucleic acid from nuclease degradation, and the like) and/or to the surface of the target epithelial cell.

By "promoter" is meant a minimal sequence sufficient to direct transcription. "Promoter" is also meant to encompass those promoter elements sufficient for promoter-dependent gene expression controllable for cell-type specific, tissue-specific or inducible by external signals or agents; such elements may be located in the 5' or 3' regions of the native gene.

By "operably linked" or "operatively linked" is meant that a DNA sequence and a regulatory sequence(s) are connected in such a way as to permit expression when the appropriate molecules (e.g., transcriptional activator proteins) are bound to the regulatory sequence(s).

By "pancreas" is meant a large, elongated, racemose gland situated transversely behind the stomach, between the spleen and the duodenum. The pancreas is composed of an endocrine portion (the pars endocrina) and an exocrine portion (the pars exocrina). The pars endocrina, which contains the islets of Langerhans, produces and secretes proteins, including insulin, directly into the blood stream. The pars exocrina contains secretory units and produces and secretes a pancreatic juice, which contains enzymes essential to protein digestion, into the duodenum.

By "euglycemia" or "euglycemic state" is meant a state associated with a level of blood glucose that is normal or nearly normal, particularly relative to the levels of blood glucose in a subject having a disease or condition associated with hyperglycemia. In humans, euglycemia correlates with blood glucose levels in the range of 70 mg/dl to 130 mg/dl.

By "precursor cell" is meant any cell which is capable of developing into an islet cell such as fetal pancreatic epithelial cells, adult pancreatic cells (e.g., pancreatic duct cells, acinar cells and pancreatic stem cells), gut epithelial cells gut stem cells or crypt cells, stem cells from other tissues (such as hematopoietic or hepatic stem cells), hepatic cells (hepatocytes and hepatic duct cells and embryonic stem cells in vivo or in vitro.

By "target cell" is meant any cell selected for incorporating DNA encoding a transcription factor nucleotide sequence such as precursor cells, fetal pancreatic epithelial cells, adult pancreatic cells (e.g., pancreatic duct cells, acinar cells and pancreatic stem cells), gut epithelial cells gut stem cells or crypt cells, stem cells from other tissues (such as hematopoietic or hepatic stem cells), hepatic cells (hepatocytes and hepatic duct cells and embryonic stem cells in vivo or in vitro.

By "islet transcription factor" is meant any transcription factor involved in the differentiation and/or development of islet cells, the expression of which contributes to the production of a cell having an islet cell phenotype, e.g., a cell that produces insulin or other markers characteristic of islet cells, as well as functionally equivalent homologues. Of particular interest are the class B basic helix-loop-helix (bHLH) transcription factors involved in the development of islet cells, which include the neurogenins (neurogenin1, neurogenin2 and neurogenin3), the neuroD factors (NeuroD1/BETA2, neuroD2, and NeuroD4/Math3) and the Mash factor, Mash1, as well as functionally equivalent homologues of these transcription factors.

By "neurogenin3 (Ngn3) regulatory pathway" is meant a transcriptionally-related group of proteins, including transcription factors, that regulate the development of pancreatic islet cells and determine the phenotype of the islet cells. A positive regulator of the Ngn3 pathway is one that promotes expression of Ngn3 or its downstream effectors and thus positively affects the induction of the islet cell phenotype. A negative regulator of the Ngn3 pathway is one that inhibits expression of Ngn3 of its downstream effectors, and thus negatively affects in the induction of the islet cell phenotype. Positive regulators include factors that inhibit activity or expression of negative regulators.

By "islet cell" is meant a cell having a phenotype similar to the hormone-producing cells normally comprising the pancreatic islets of Langerhans, and generally characterized by the expression of markers that normally distinguishing the cells in the pancreatic islets of Langerhans from other pancreatic cells, such as insulin, glucagon, somatostatin, pancreatic polypeptide, or islet amyloid polypeptide.

By "β cell" is meant a pancreatic islet cell having a phenotype characterized by the expression of markers that normally distinguish the beta-cells from the other pancreatic islets cells, such as insulin, Nkx6.1 or glucokinase.

By "α cell" is meant a pancreatic islet cell having a phenotype characterized by the expression of markers that normally distinguish the α-cells from the other pancreatic islets cells, such as proglucagon or glucagons.

By "target cell" is meant a cell in which, for example, introduction of a nucleic acid of interest of expression is desired. The use of "target cell" throughout the specification is for convenience only, and is not meant to imply that, for example, accomplishing introduction of a nucleic acid of interest requires the use of targeting techniques (e.g., targeting molecules that preferentially direct the material to be introduced to a particular cell or cell type).

By "subject" or "patient" is meant any mammalian subject for whom diagnosis or therapy is desired, particularly humans. Other subjects may include cattle, dogs, cats, guinea pigs, rabbits, rats, mice, horses, and so on. Of particular interest are subjects having an insulin-associated disorder that is amenable to treatment (e.g., to mitigate symptoms associated with the disorder) by expression of either a islet transcription factor-encoding nucleic acid in a cell of the subject (e.g., by introduction of a islet transcription factor-encoding nucleic acid into the subject in vivo, or by implanting cells expressing a islet transcription factor (e.g., β-cell precursors) or nearly developed or mature β-cells cultured from cells expressing a islet transcription factor into the subject, which cells produce insulin).

For sake of clarity, the following table provides a cross-reference of names of transcription factors as used in the present specification with names of the same factors as referred to in the literature as well as the official name of the corresponding human gene.

| Name as used herein | Other names in the literature | Official human gene name* |
|---|---|---|
| neurogenin1 | ngn1; amth4C; neuroD3 | NEUROG1 |
| neurogenin2 | ngn2; math4A; ATOH4 | NEUROG2 |
| neurogenin3 | ngn3; math4B; ATOH5; relax | NEUROG3 |
| neuroD1 | BETA2; BHF1; neuroD | NEUROD1 |
| neuroD2 | NDRF; rat4; KW8 | NEUROD2 |
| neuroD4 | math3; neuroM; ath3; ATOH3 | NEUROD4 |
| math2 | ath2; nex1; dlx3; atoh6 | NEUROD6 |
| mash1 | ASH1; HASH1 | ASCL1 |
| mash2 | ASH2; HASH2 | ASCL2 |
| math1 | HATH1 | ATOH1 |

*As accepted by the Human Gene Nomenclature Committee.

Overview of the Invention

The present invention is based upon the discovery that the introduction of a polynucleotide sequence encoding an islet transcription factor into a pancreatic cell or other appropriate cell induces the production of cells having the phenotype of pancreatic islet cells, including insulin-producing β-cells. This discovery in turn is based on the discovery that providing for increased neurogenin3 (Ngn3) activity in a mature pancreatic cell (a non-beta cell), provides for development of the non-beta pancreatic cell into a cell with the pancreatic beta cell phenotype (e.g., production of insulin).

An increase in Ngn3 activity can be accomplished by, for example, introducing an Ngn3-encoding polynucleotide into a cell to provide for Ngn3 expression (which may be in addition to endogenous Ngn3 expression in the cell); providing for increased levels of expression of a positive regulator of Ngn3 (e.g., by introducing a polynucleotide encoding a transcription factor that positively regulates Ngn3 expression, or otherwise increasing activity or expression of such Ngn3 positive regulators); inhibiting activity (e.g., by inhibiting expression) of a negative regulator or inhibitor of Ngn3 expression or activity); increasing expression of a downstream effector which is positively regulated by Ngn3; and other variations that will be readily apparent to the ordinarily skilled artisan upon reading the present specification. Modulating of transcription factor activity (e.g., increasing Ngn3 activity or decreasing activity of an inhibitor of Ngn3 expression) can also be accomplished by use of signaling molecules (receptors, ligands, intracellular effectors), as well as synthetic and natural small molecule regulators of the pathway.

The invention generally involves providing for increased expression of at least one islet transcription factor selected from the neurogenic basic helix-loop-helix factors (bHLH) including the neurogenins (neurogenin1/NEUROG1/MATH4C/NeuroD3, neurogenin2/NEUROG2/MATH4A or neurogenin3/NEUROG3/MATH4B), the neuroD factors (NeuroD1/BETA2/BHF1, NeuroD2/NDRF, MATH2/NEX1/DLX3, NeuroD4/Math3), the Mash factors (Mash1 and Mash2), and the atonal-related factors (MATH1/ATOH1), as well as combinations thereof or combinations with other genes, to provide for induction of pancreatic beta cells.

Figure 10:
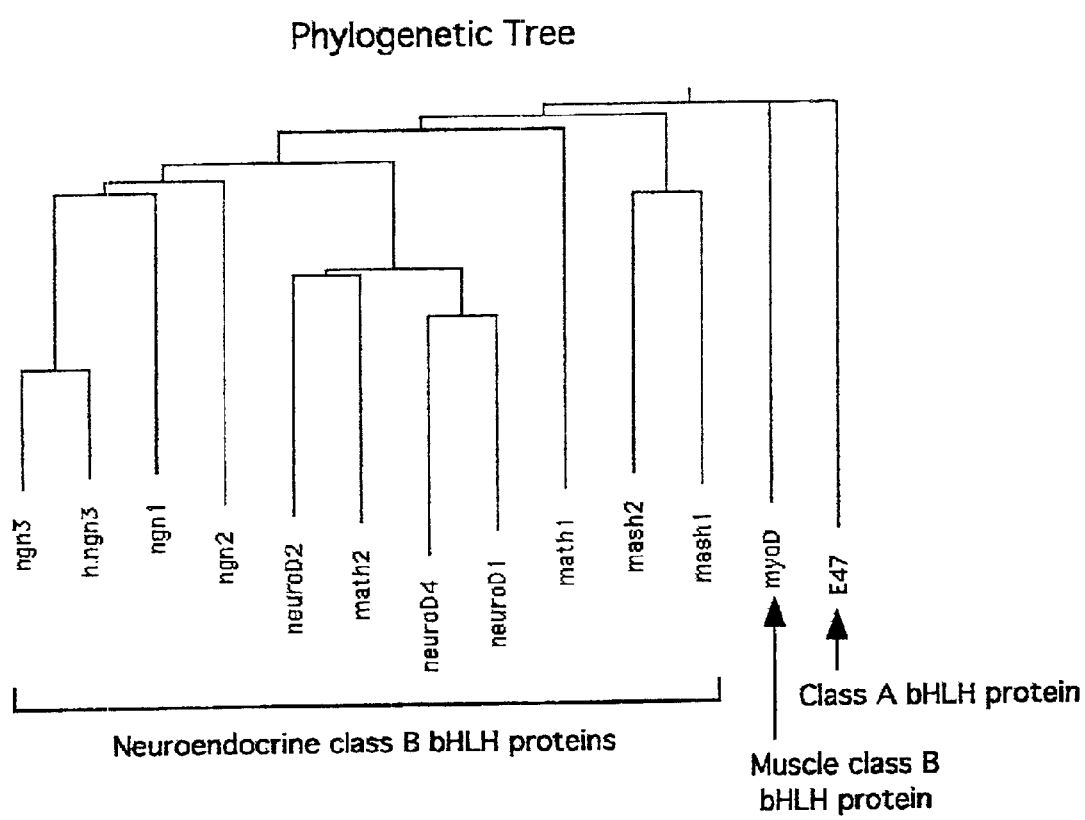
FIG. 10 is a graphical representation of the phylogenetic tree of bHLH proteins. All sequences are mouse except h.ngn3 which is human.

FIG. 10 is a schematic representation of an alignment tree for neuroendorcrine bHLH proteins, plus myoD (a myogenic class B bHLH protein, and E47 (class A (ubiquitous) bHLH protein). All are based on mouse amino acid sequences. The sequences were aligned using the multiple sequence alignment algorithm Clustal-W as supplied in the MacVector6.5.1 sequence analysis program (Oxford Molecular). The definition of class A and B is based on the classification of Murre et al. (Murre, et al. (1989) Cell 58(3), 537–44).

Islet transcription factors are involved in the differentiation and development of islet cells. Islet transcription factors include members of the class B basic helix-loop-helix (bHLH) family of transcription factors, a family of factors known to regulate growth and differentiation of numerous cell types. Islet cells and the developing pancreas express a broad group of class B bHLH genes, among the most abundant being Ngn3, NeuroD1/BETA2, Mash1 and NeuroD4/Math3. NeuroD1 is also known as BETA2 and has been shown to be involved in the early differentiation of islet cells and the regulation of insulin transcription in pancreatic beta cells. Neurogenin3 activates NeuroD1/BETA2 during pancreatic development and therefore neurogenin3 lies upstream of neuroD1 in the hierarchy of islet transcription factors activated during islet cell differentiation. Ngn3 is expressed in islet cell progenitors and functions as a pro-endocrine gene, driving islet cell differentiation. Ngn3 is expressed early on in the development of all four islet cell types and is involved in the regulation of other islet transcription factors such as Pax4 and Nkx2.2 as well as NeuroD1/BETA1. Early and ectopic expression of Ngn3 can cause early and ectopic differentiation of islet cells. Other islet transcription factors also include non-bHLH factors such as the homeodomain factors, e.g. Nkx2.2 and Nkx6.1. These factors are immediately upstream or downstream of ngn3 and are involved in islet cell development. The pou-homeodomain factor HNF1 and the winged-helix factor HNF3 lie upstream of ngn3, and along with the cut-homeodomain factor HNF6 have been implicated in islet cell differentiation and are further examples of islet transcription factors in accordance to the present invention.

While Ngn3 is referred to throughout the specification, such reference is not intended to be limiting. Rather Ngn3 is only exemplary of islet transcription factors useful in the invention, and reference to it alone is for clarity and ease in review of the specification.

Induction of Beta-Cell Development

Pancreatic beta-cells can be produced from non-beta cell pancreatic cells by providing for production of an islet transcription factor in a pancreatic cell either in vivo (e.g., by administration of islet transcription factor-encoding nucleic acid (e.g., RNA or DNA) to the pancreas of a subject, e.g., by introduction of nucleic acid into a lumen of a pancreatic duct), or in vitro, e.g., by contacting a target cell (e.g., an isolated, non-beta, pancreatic cell) with islet transcription factor-encoding nucleic acid (e.g., RNA or DNA) in culture (which cells are then cultured, expanded, and transplanted into a subject).

In one embodiment of particular interest, beta cells are produced by providing for expression of neurogenin3 (Ngn3) at a level sufficient to induce the beta cell phenotype in the target cell. Expression of Ngn3 in the target cell can be accomplished in a variety of ways. For example, in one embodiment, Ngn3 expression is accomplished by introduction of Ngn3-encoding nucleic acid (e.g., DNA or RNA) to provide for expression of the encoded Ngn3 polypeptide in the target cell). In another embodiment Ngn3 expression is induced by introduction of a gene encoding a protein that provides for induction of Ngn3 expression (e.g., expression of an "upstream" positive regulator of Ngn3 expression in the target cell). In another embodiment, Ngn3 expression is accomplished by introduction of a gene encoding a protein that inhibits activity (e.g., function or expression) a negative regulator of Ngn3 expression. In another embodiment Ngn3 expression is induced by introduction of a small molecule that provides for induction of Ngn3 expression (e.g., a small molecule pharmaceutical that induces Ngn3 expression in the target cell). In addition, production of pancreatic beta cells of the invention can also be accomplished by providing for production of factors induced by Ngn3.

As will be readily appreciated by the ordinarily skilled artisan upon reading the present disclosure, Ngn3 expression can be accomplished by providing for any combination of these approaches. For example, the invention also encompasses providing for expression in the target cell of both an Ngn3-encoding nucleic acid as well as a positive regulator of an endogenous Ngn3 gene; providing for expression of an introduced Ngn3 nucleic acid as well as an inhibitor of a negative regulator of an endogenous Ngn3 and introduced Ngn3 sequence; and the like. In general, any combination of the approaches that provide for Ngn3 activity by, for example, providing for expression of Ngn3 per se (by introduction of Ngn3-encoding nucleic acid or providing for expression of endogenous Ngn3) and/or by providing of production of factors "downstream" of Ngn3 that are normally produced as a result of Ngn3 expression, are within the scope of the present invention. Positive regulators of Ngn3 expression include, but are not necessarily limited to HNF1, HNF3, and HNF6.

In general, factors that provide for production of Ngn3 activity in a target cell are referred to herein as "islet transcript factors." As noted above "islet transcription factor" is meant any transcription factor involved in the differentiation and/or development of islet cells, the expression of which contributes to the production of a cell having an islet cell phenotype, e.g., a cell that produces insulin or other markers characteristic of islet cells, as well as functionally equivalent homologues. Of particular interest are the class B basic helix-loop-helix (bHLH) transcription factors involved in the development of islet cells, which include the neurogenins (neurogenin1, neurogenin2 and neurogenin3), the neuroD factors (NeuroD1/BETA2, neuroD2, and NeuroD4/Math3) and the Mash factor, Mash1, as well as functionally equivalent homologues of these transcription factors. Reference to Ngn3 herein is for clarity, and is not meant to be limiting, but rather to provide a reference point in a regulatory pathway that leads to pancreatic beta cell development.

In addition, induction of the activity of the Ngn3 pathway can be accomplished using naturally occurring or synthetic molecules other than nucleic acid. For example, Ngn3 activity can be induced by using a synthetic molecule that promotes Ngn3 expression, e.g., by inhibiting activity of a negative regulator of Ngn3 expression. Inhibitory transcription factors of Ngn3 expression include, but are not necessarily limited to HES1. Negative signally pathways that inhibit Ngn3 expression include, but are not necessarily limited to, the Notch pathway.

Islet Transcription Factor Nucleic Acids

The term "islet transcription factor gene" is used to designate both transcription factors that are expressed in pancreatic islet cells, and also transcription factors that are involved in the development, differentiation, or formation of islet cells. The term "islet transcription factor gene" is also intended to mean the open reading frame encoding specific islet transcription factor polypeptides, introns, and adjacent 5' and 3' non-coding nucleotide sequences involved in the regulation of expression), up to about 10 kb beyond the coding region, but possibly further in either direction. The DNA sequences encoding an islet transcription factor may be cDNA or genomic DNA or a fragment thereof. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing, to create a continuous open reading frame encoding the polypeptide of interest.

A islet transcription factor genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 10 kb, but possibly more, of flanking genomic DNA at either the 5' or 3' end of the transcribed region. The genomic DNA may be isolated as a large fragment of 100 kbp or more, or as a smaller fragment substantially free of flanking chromosomal sequence.

The sequence of this 5' region, and further 5' upstream sequences and 3' downstream sequences, may be utilized for promoter elements, including enhancer binding sites, that provide for expression in tissues where the islet transcription factor is expressed. The sequences of the islet transcription factor promoter elements of the invention can be based on the nucleotide sequences of any species (e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably mouse or human) and can be isolated or produced from any source whether natural, synthetic, semi-synthetic or recombinant.

The nucleic acid compositions used in the subject invention may encode all or a part, usually at least substantially all, of the islet transcription factor polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least about ten contiguous nucleotides, usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The islet transcription factor genes are isolated and obtained in substantial purity, generally as other than an intact mammalian chromosome. Usually, the DNA will be obtained substantially free of other nucleic acid sequences that do not include a sequence encoding an islet transcription factor or fragment thereof, generally being at least about 50%, usually at least about 90% pure and are typically "recombinant", i.e. flanked by one or more nucleotides with which it is not normally associated on a naturally occurring chromosome.

The sequence of the islet transcription factor, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two, or by at least about ten or more nucleotides or amino acids. In general, the sequence changes may be substitutions, insertions or deletions. Deletions may further include larger changes, such as deletions of a domain or exon. It should be noted that islet transcription factor sequences are conversed mainly within the bHLH domain, and regions outside this domain may not be as well-conserved, and may even be remarkably poorly conserved, between, for example, rat, mouse, and humans. Thus islet transcription factors can tolerate more nucleotide and amino acid residue changes outside of the bHLH domain and retain function to a much greater extent than changes made within the bHLH domain. Such modified islet transcription factor sequences can be used, for example, to generate vectors for introduction into target cells for the purpose of producing islet cells.

Techniques for in vitro mutagenesis of cloned genes are known. Examples of protocols for scanning mutations may be found in Gustin et al., 1993 Biotechniques 14:22; Barany, 1985 Gene 37:111–23; Colicelli et al., 1985 Mol Gen Genet 199:537–9; and Prentki et al., 1984 Gene 29:303–13. Methods for site specific mutagenesis can be found in Sambrook et al., 1989 Molecular Cloning: A Laboratory Manual, CSH Press, pp. 15.3–15.108; Weiner et al., 1993 Gene 126:35–41; Sayers et al., 1992 Biotechniques 13:592–6; Jones and Winistorfer, 1992 Biotechniques 12:528–30; Barton et al., 1990 Nucleic Acids Res 18:7349–55; Marotti and Tomich, 1989 Gene Anal Tech 6:67–70; and Zhu 1989 Anal Biochem 177:120–4.

An islet transcription factor of particular interest in the present invention is a member of the neurogenin transcription factor family, e.g., neurogenin 1 (Ngn1), neurogenin2 (Ngn2), neurogenin 3 (Ngn3), with Ngn3 being of particular interest. The nucleotide and amino acid sequences of human Ngn3 are provided in the Sequence Listing as SEQ ID NOS: 1 and 2, respectively. The nucleotide and amino acid sequences of human Ngn1 are available at GenBank accession number XM_003834 and NM_006161. The nucleotide and amino acid sequence of human Ngn2 are available at GenBank accession number AF303002.

It should be noted that transcription factors which act either "upstream" of ngn3 (and therefore activate ngn3 expression) or "downstream" of Ngn3, that lead to development of the islet cell phenotype, are also contemplated for use in the present invention.

Neurogenin3 by itself, is sufficient to force undifferentiated pancreatic epithelial cells to become islet cells. Since neurogenin3 expression determines which precursor cells will differentiate into islet cells, the signals that regulate neurogenin3 expression are also involved in islet cell formation. Although 2.7 kb of the ngn3 promoter is sufficient to direct expression correctly in transgenic mice, distal sequences have been shown to greatly enhance the expression of ngn3. This distal promoter region contains a cluster of binding sites for pancreatic transcription factors such as, HNF6, HNF1α, and HNF3β. These pancreatic transcription factors have been found to regulate ngn3 gene expression and thereby are also involved in the control of islet cell formation. These signals may be useful in generating new islet cells for patients with diabetes mellitus.

In another embodiment, the islet transcription factor is human NeuroD1/BETA2 gene, which is available, with the corresponding human NeuroD1/BETA2 amino acid sequence, at GenBank accession number NM_002500.

The human Mash1gene and the corresponding amino acid sequence are available at GenBank accession number XM_006688.

The human NeuroD4/Math3 gene and the corresponding human NeuroD4/Math3 amino acid sequence are available at GenBank accession number AF203901.

Constructs for Delivery of Islet Transcription Factor Nucleic Acid

Where the islet transcription factor nucleic acid to be delivered is DNA, any construct having a promoter (e.g., a promoter that is functional in a eukaryotic cell) operably linked to a DNA of interest can be used in the invention. The constructs containing the DNA sequence (or the corresponding RNA sequence) which may be used in accordance with the invention may be any eukaryotic expression construct containing the DNA or the RNA sequence of interest. For example, a plasmid or viral construct (e.g. adenovirus) can be cleaved to provide linear DNA having ligatable termini. These termini are bound to exogenous DNA having complementary-like ligatable termini to provide a biologically functional recombinant DNA molecule having an intact replicon and a desired phenotypic property. Preferably the construct is capable of replication in eukaryotic and/or prokaryotic hosts (viruses in eukaryotic, plasmids in prokaryotic), which constructs are known in the art and are commercially available.

The constructs can be prepared using techniques well known in the art. Likewise, techniques for obtaining expression of exogenous DNA or RNA sequences in a genetically altered host cell are known in the art (see, for example, Kormal et al., *Proc. Natl. Acad. Sci. USA*, 84:2150–2154, 1987; Sambrook et al. Molecular Cloning: a Laboratory Manual, 2nd Ed., 1989, Cold Spring Harbor Laboratory Press, Cold Spring Harbor, N.Y., each of which are hereby incorporated by reference with respect to methods and compositions for eukaryotic expression of a DNA of interest).

In one embodiment, the DNA construct contains a promoter to facilitate expression of the DNA of interest within a pancreatic cell. The promoter may be a strong, viral promoter that functions in eukaryotic cells such as a promoter from cytomegalovirus (CMV), mouse mammary tumor virus (MMTV), Rous sarcoma virus (RSV), or adenovirus. More specifically, exemplary promoters include the promoter from the immediate early gene of human CMV (Boshart et al., *Cell* 41:521–530, 1985) and the promoter from the long terminal repeat (LTR) of RSV (Gorman et al., *Proc. Natl. Acad. Sci. USA* 79:6777–6781, 1982). Of these two promoters, the CMV promoter is presently preferred as it provides for higher levels of expression than the RSV promoter.

Alternatively, the promoter used may be a strong general eukaryotic promoter such as the actin gene promoter. In one embodiment, the promoter used may be a tissue-specific promoter. For example, the promoter used in the construct may be a pancreas specific promoter, a duct cell specific promoter or a stem cell specific promoter. The constructs of the invention may also include sequences in addition to promoters which enhance expression in the target cells.

In another embodiment, the promoter is a regulated promoter, such as a tetracycline-regulated promoter, expression from which can be regulated by exposure to an exogenous substance (e.g., tetracycline.).

Other components such as a marker (e.g., an antibiotic resistance gene (such as an ampicillin resistance gene) or β-galactosidase) aid in selection or identification of cells containing and/or expressing the construct, an origin of replication for stable replication of the construct in a bacterial cell (preferably, a high copy number origin of replication), a nuclear localization signal, or other elements which facilitate production of the DNA construct, the protein encoded thereby, or both.

For eukaryotic expression, the construct should contain at a minimum a eukaryotic promoter operably linked to a DNA of interest, which is in turn operably linked to a polyadenylation signal sequence. The polyadenylation signal sequence may be selected from any of a variety of polyadenylation signal sequences known in the art. An exemplary polyadenylation signal sequence is the SV40 early polyadenylation signal sequence. The construct may also include one or more introns, where appropriate, which can increase levels of expression of the DNA of interest, particularly where the DNA of interest is a cDNA (e.g., contains no introns of the naturally-occurring sequence). Any of a variety of introns known in the art may be used (e.g., the human β-globin intron, which is inserted in the construct at a position 5' to the DNA of interest).

In an alternative embodiment, the nucleic acid delivered to the cell is an RNA encoding an islet transcription factor. In this embodiment, the RNA is adapted for expression (i.e., translation of the RNA) in a target cell. Methods for production of RNA (e.g., mRNA) encoding a protein of interest are well known in the art, and can be readily applied to the product of RNA encoding islet transcription factors useful in the present invention.

Delivery of Islet Transcription Factor-Encoding Nucleic Acid

Delivery of islet transcription factor-encoding nucleic acid can be accomplished using a viral or a non-viral vector. In one embodiment the nucleic acid is delivered within a viral particle, such as an adenovirus. In another embodiment, the nucleic acid is delivered in a formulation comprising naked DNA admixed with an adjuvant such as viral particles (e.g., adenovirus) or cationic lipids or liposomes. An "adjuvant" is a substance that does not by itself produce the desired effect, but acts to enhance or otherwise improve the action of the active compound. The precise vector and vector formulation used will depend upon several factors, such as the size of the DNA to be transferred, the delivery protocol to be used, and the like. Exemplary non-viral and viral vectors are described in more detail below.

I. Viral Vectors

In general, viral vectors used in accordance with the invention are composed of a viral particle derived from a naturally-occurring virus which has been genetically altered to render the virus replication-defective and to deliver a recombinant gene of interest for expression in a target cell in accordance with the invention.

Numerous viral vectors are well known in the art, including, for example, retrovirus, adenovirus, adeno-associated virus, herpes simplex virus (HSV), cytomegalovirus (CMV), vaccinia and poliovirus vectors. Adenovirus and AAV are usually preferred viral vectors since these viruses efficiently infect slowly replicating and/or terminally differentiated cells. The viral vector may be selected according to its preferential infection of the cells targeted.

Where a replication-deficient virus is used as the viral vector, the production of infectious virus particles containing either DNA or RNA corresponding to the DNA of interest can be achieved by introducing the viral construct into a recombinant cell line which provides the missing components essential for viral replication. In one embodiment, transformation of the recombinant cell line with the recombinant viral vector will not result in production or substantial production of replication-competent viruses, e.g., by homologous recombination of the viral sequences of the recombinant cell line into the introduced viral vector. Methods for production of replication-deficient viral particles containing a nucleic acid of interest are well known in the art and are described in, for example, Rosenfeld et al., *Science* 252:431–434, 1991 and Rosenfeld et al., *Cell* 68:143–155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus). Methods and materials for manipulation of the mumps virus genome, characterization of mumps virus genes responsible for viral fusion and viral replication, and the structure and sequence of the mumps viral genome are described in Tanabayashi et al., *J. Virol.* 67:2928–2931, 1993; Takeuchi et al., *Archiv. Virol.,* 128:177–183, 1993; Tanabayashi et al., *Virol.* 187:801–804, 1992; Kawano et al., *Virol.,* 179:857–861, 1990; Elango et al., *J. Gen. Virol.* 69:2893–28900, 1988.

II. Non-viral Vectors

The nucleic acid of interest may be introduced into a cell using a non-viral vector. "Non-viral vector" as used herein is meant to include naked DNA (e.g., DNA not contained within a viral particle, and free of a carrier molecules such as lipids), chemical formulations comprising naked nucleic acid (e.g., a formulation of DNA (and/or RNA) and cationic compounds (e.g., dextran sulfate, cationic lipids)), and naked nucleic acid mixed with an adjuvant such as a viral particle (e.g., the DNA of interest is not contained within the viral particle, but the formulation is composed of both naked DNA and viral particles (e.g., adenovirus particles) (see, e.g., Curiel et al. 1992 Am. J. Respir. Cell Mol. Biol. 6:247–52). Thus "non-viral vector" can include vectors composed of nucleic acid plus viral particles where the viral particles do not contain the DNA of interest within the viral genome.

In one embodiment, the formulation comprises viral particles which are mixed with the naked DNA construct prior to administration. About $10^8$ to about $10^{10}$ viral particles (preferably about $1\times10^{10}$ to about $5\times10^{10}$, more preferably about $3\times10^{10}$ particles) are mixed with the naked DNA construct (about 5 $\mu$g to 50 $\mu$g DNA, more preferably about 8 $\mu$g to 25 $\mu$g DNA) in a total volume of about 100 $\mu$l. Preferably the viral particles are adenovirus particles (Curiel et al., 1992 supra).

Alternatively or in addition, the nucleic acid can be complexed with polycationic substances such as poly-L-lysine or DEAC-dextran, targeting ligands, and/or DNA binding proteins (e.g., histones). DNA- or RNA-liposome complex formulations comprise a mixture of lipids which bind to genetic material (DNA or RNA) and facilitate delivery of the nucleic acid into the cell. Liposomes which can be used in accordance with the invention include DOPE (dioleyl phosphatidyl ethanol amine), CUDMEDA (N-(5-cholestrum-3-.beta.-ol 3-urethanyl)-N',N'-dimethylethylene diamine).

For example, the naked DNA can be administered in a solution containing Lipofectin™ (LTI/BRL) at a concentrations ranging from about 2.5% to 15% volume: volume, preferably about 6% to 12% volume:volume. Preferred methods and compositions for formulation of DNA for delivery according to the method of the invention are described in U.S. Pat. No. 5,527,928, the disclosure of which is incorporated herein by reference.

The nucleic acid of interest can also be administered as a chemical formulation of DNA or RNA coupled to a carrier molecule (e.g., an antibody or a receptor ligand) which facilitates delivery to host cells for the purpose of altering the biological properties of the host cells. By the term "chemical formulations" is meant modifications of nucleic acids which allow coupling of the nucleic acid compounds to a carrier molecule such as a protein or lipid, or derivative thereof. Exemplary protein carrier molecules include antibodies specific to the cells of a targeted pancreatic cell or receptor ligands, e.g., molecules capable of interacting with receptors associated with a cell of a targeted pancreatic cell.

Production of Islet Transcription Factor Polypeptides and Antibodies that Specifically Bind such Polypeptides Nucleic acid encoding Ngn3 or other islet transcription factors of interest may be employed to synthesize full-length polypeptides or fragments thereof, particularly fragments corresponding to functional domains; DNA binding sites; etc.; and including fusions of the subject polypeptides to other proteins or parts thereof. Accordingly, the polynucleotides and polypeptides suitable for use in the invention include, without limitation, islet transcription factor polypeptides and polynucleotides found in primates, rodents, canines, felines, equines, nematodes, yeast and the like, and the natural and non-natural variants thereof.

The islet transcription factor polypeptides can be used for the production of antibodies, where short fragments provide for antibodies specific for the particular polypeptide, and larger fragments or the entire protein allow for the production of antibodies over the surface of the polypeptide. Antibodies may be raised to the wildtype or variant forms of the polypeptide. Antibodies may be raised to isolated peptides corresponding to these domains, or to the native protein, e.g. by immunization with cells expressing the polypeptide of interest, immunization with liposomes having a polypeptide of interest inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. For further description, see Monoclonal Antibodies: A Laboratory Manual, Harlow and Lane eds., Cold Spring Harbor Laboratories, Cold Spring Harbor, N.Y., 1988.

Antibodies that specifically bind islet transcription factors can be utilized to detect cells expressing a recombinant islet transcription factor such as Ngn3 (e.g., prior to transplantation).

Production of Islet Cells by Expression of Transcription Factor-Encoding Nucleic Acids Islet cells can be produced according to the invention in a variety of ways. In general, the invention involves stimulating the production of an islet transcription factor. In an embodiment of particular interest, the invention involves enhancing islet transcription factor activity by introducing a nucleic acid encoding an islet transcription factor into a cell, usually a pancreatic cell.

I. Production of Islet Cells In Vitro by Introduction of an Islet Transcription Factor-Encoding Nucleic Acid Nucleic acid encoding an islet transcription factor (e.g., Ngn3) can be introduced into a cell in vitro to accomplish expression in the cell to provide for at least transient expression. The cells into which the nucleic acid is introduced can be differentiated epithelial cells (e.g., pancreatic cells, gut cells, hepatic cells or duct cells), pluripotent adult or embryonic stem cells, or any mammalian cell capable of developing into β cells or cells capable of expression of insulin in vitro following expression of an islet transcription factor-encoding nucleic acid. The cell is subsequently implanted into a subject having a disorder characterized by a deficiency in insulin, which disorder is amenable to treatment by islet cell replacement therapy. In one embodiment, the host cell in which Ngn3 expression is provided and which is implanted in the subject is derived from the individual who will receive the transplant (e.g., to provide an autologous transplant). For example, in a subject having Type 1 diabetes, pluripotent stem cells, hepatic cells, gut cells or pancreatic cells can be isolated from the affected subject, the cells modified to express Ngn3-encoding DNA, and the cells implanted in the affected subject to provide for insulin production, or the transformed cells cultured so as to facilitate development of the cells into insulin-producing β-cells. Alternatively, pluripotent stem cells, hepatic cells, gut cells or pancreatic cells from another subject (the "donor") could be modified to express Ngn3-encoding DNA, and the cells subsequently implanted in the affected subject to provide for insulin production, or the transformed cells cultured so as to facilitate development of the cells into insulin-producing β-cells.

Introduction of nucleic acid into the cell in vitro can be accomplished according to methods well known in the art (e.g., through use of electroporation, microinjection, lipofection infection with a recombinant (preferably replication-deficient) virus, and other means well known in the art). The nucleic acid is generally operably linked to a promoter that facilitates a desired level of polypeptide expression (e.g., a promoter derived from CMV, SV40, adenovirus, or a tissue-specific or cell type-specific promoter). Transformed cells containing the recombinant nucleic acid can be selected and/or enriched via, for example, expression of a selectable marker gene present in the introduced construct or that is present on a nucleic acid that is co-transfected with the construct. Typically selectable markers provide for resistance to antibiotics such as tetracycline, hygromycin, neomycin, and the like. Other markers can include thymidine kinase and the like. Other markers can include markers that can be used to identify expressing cells, such as beta-galactosidase or green florescent protein.

Expression of the introduced nucleic acid in the transformed cell can be assessed by various methods known in the art. For example, expression of the introduced gene can be examined by Northern blot to detect mRNA which hybridizes with a DNA probe derived from the relevant gene. Those cells that express the desired gene can be further isolated and expanded in in vitro culture using methods well known in the art. The host cells selected for transformation will vary with the purpose of the ex vivo therapy (e.g., insulin production), the site of implantation of the cells, and other factors that will vary with a variety of factors that will be appreciated by the ordinarily skilled artisan.

The transformed cell can also be examined for the development of an islet cell phenotype. For example, expression of insulin could be detected by PCR, northern blot, immunocytochemistry, western blot. RIA or ELISA Alternatively a marker gene such as green florescent protein or an antibiotic resistance gene operatively linked to an islet specific promoter such as the insulin gene promoter could be used for identification or selection of differentiated islet cells. Methods for engineering a host cell for expression of a desired gene product(s) and implantation or transplantation of the engineered cells (e.g., ex vivo therapy) are known in the art (see, e.g., Gilbert et al. 1993 "Cell transplantation of genetically altered cells on biodegradable polymer scaffolds in syngeneic rats," Transplantation 56:423–427). For expression of a desired gene in exogenous or autologous cells and implantation of the cells (e.g., islet cells) into pancreas, see, e.g., Docherty 1997 "Gene therapy for diabetes mellitus," Clin Sci (Colch) 92:321–330; Hegre et al. 1976 "Transplantation of islet tissue in the rat," Acta Endocrinol Suppl (Copenh) 205:257–281; Sandler et al. 1997 "Assessment of insulin secretion in vitro from microencapsulated fetal porcine islet-like cell clusters and rat, mouse, and human pancreatic islets," Transplantation 63:1712–1718; Calafiore 1997 "Perspectives in pancreatic and islet cell transplantation for the therapy of IDDM," Diabetes Care 20:889–896; Kenyon et al. 1996 "Islet cell transplantation: beyond the paradigms," Diabetes Metab Rev 12:361–372; Sandler; Chick et al. 1977 Science "Artificial pancreas using living beta cells: effects on glucose homeostasis in diabetic rats," 197:780–782. In general, the cells can be implanted into the pancreas, or to any practical or convenient site, e.g., subcutaneous site, liver, peritoneum.

Methods for transplanting islets cells are well known in the art, see, e.g., Hegre et al. 1976 "Transplantation of islet tissue in the rat," Acta Endocrinol Suppl (Copenh) 205:257–281; Sandler et al. 1997 "Assessment of insulin secretion in vitro from microencapsulated fetal porcine islet-like cell clusters and rat, mouse, and human pancreatic islets," Transplantation 63:1712–1718; Calafiore 1997 "Perspectives in pancreatic and islet cell transplantation for the therapy of IDDM," Diabetes Care 20:889–896; Kenyon et al. 1996 "Islet cell transplantation: beyond the paradigms," Diabetes Metab Rev 12:361–372; Sandler; Chick et al. 1977 Science "Artificial pancreas using living beta cells: effects on glucose homeostasis in diabetic rats," 197:780–782.

In general, after expansion of the transformed cells in vitro, the cells are implanted into the mammalian subject by methods well known in the art. The number of cells implanted is a number of cells sufficient to provide for expression of levels of insulin sufficient to lower blood glucose levels. The number of cells to be transplanted can be determined based upon such factors as the levels of polypeptide expression achieved in vitro, and/or the number of cells that survive implantation. The transformed cells are implanted in an area of dense vascularization such as the liver, and in a manner that minimizes surgical intervention in the subject. The engraftment of the implant of transformed cells is monitored by examining the mammalian subject for classic signs of graft rejection, i.e., inflammation and/or exfoliation at the site of implantation, and fever, and by monitoring blood glucose levels.

The transplantation method described above is not limited to the expression of nerougenin3. Engineering a host cell for expression of other islet transcription factors in the differentiation cascade, such as islet factors and in particular, NeuroD1/BETA2 may be beneficial to subjects with insulin deficiencies.

II. In Vivo Development of Islet Cells and Production of Insulin in the Pancreas Islet transcription factor-encoding nucleic acid can be delivered directly to a subject to provide for islet transcription factor expression in a target cell (e.g., a pancreatic cell, gut cell, liver cell, or other organ cell capable of expressing an islet transcription factor and providing production of insulin), thereby promoting development of the cell into an insulin-producing cell (e.g., in pancreas) or to cure a defect in islet transcription factor expression in the subject. Methods for in vivo delivery of a nucleic acid of interest for expression in a target cell are known in the art. For example, in vivo methods of gene delivery normally employ either a biological means of introducing the DNA into the target cells (e.g., a virus containing the DNA of interest) or a mechanical means to introduce the DNA into the target cells (e.g., direct injection of DNA into the cells, liposome fusion, or pneumatic injection using a gene gun).

In general, the transformed cells expressing the protein encoded by the DNA of interest produce a therapeutically effective amount of the protein to produce islet cells, in particular β-cells in the mammalian patient. In one embodiment, the DNA of interest encodes an islet transcription factor such as Neurogenin1, Neurogenin2, Neurogenin3, NeuroD1/BETA2, Mash1 or NeuroD4/Math3 (with Ngn3 being of particular interest), and the DNA of interest is operably linked to a promoter, which may be heterologous or endogenous to the transcription factor.

In general terms, the delivery method comprises introducing the nucleic of interest-containing vector into a pancreatic cell. By way of example, DNA of interest-containing vector may comprise either a viral or non-viral vector (including naked DNA), which is introduced into the pancreas in vivo via the duct system. Intraductal administration can be accomplished by cannulation by, for example, insertion of the cannula through a lumen of the gastrointestinal tract, by insertion of the cannula through an external orifice, or insertion of the cannula through the common bile duct. Retrograde ductal administration may be accomplished in the pancreas by endoscopic retrograde chalangiopancreatography (ECRP). Exemplary methods for accomplishing intraductal delivery to the pancreas are described in U.S. Pat. No. 6,004,944.

The precise amount of islet transcription factor-encoding nucleic acid administered will vary greatly according to a number of factors including the susceptibility of the target cells to transformation, the size and weight of the subject, the levels of protein expression desired, and the condition to be treated. The amount of nucleic acid and/or the number of infectious viral particles effective to infect the targeted tissue, transform a sufficient number of cells, and provide for production of a desired level of insulin can be readily determined based upon such factors as the efficiency of the transformation in vitro and the susceptibility of the targeted cells to transformation. For example, the amount of DNA introduced into the pancreatic duct of a human is, for example, generally from about 1 µg to about 750 mg, preferably from about 500 µg to about 500 mg, more preferably from about 10 mg to about 200 mg, most preferably about 100 mg. Generally, the amounts of DNA can be extrapolated from the amounts of DNA effective for delivery and expression of the desired gene in an animal model. For example, the amount of DNA for delivery in a human is roughly 100 times the amount of DNA effective in a rat.

Pancreatic cells modified according to the invention can facilitate sufficiently high levels of expression of a nucleic acid of interest, particularly where the nucleic acid delivered is DNA and the DNA of interest is operably linked to a strong eukaryotic promoter (e.g., CMV, MMTV). The expressed protein can induce islet cell and insulin production. Thus the methods of the invention are useful in treating a mammalian subject having a variety of insulin related conditions.

In the preferred embodiment, the encoded proteins are islet transcription factors from the class of basic helix-loop-helix (bHLH) proteins. For example, the expression of neurogenin3 and/or NeuroD1/BETA2 may substantially induce the production of islet cells and insulin in mammals.

The actual number of transformed pancreatic cells required to achieve therapeutic levels of the protein of interest will vary according to several factors including the protein to be expressed, the level of expression of the protein by the transformed cells, the rate in which the protein induces islet cell production (in particular Beta cells), and the condition to be treated.

Regardless of whether the islet transcription factor-encoding nucleic acid is introduced in vivo or ex vivo, the nucleic acid (or islet cells produced in vitro or recombinant cells expressing the islet transcription factor nucleic acid that are to be transplanted for development into islet cells in vivo post-transplantation) can be administered in combination with other genes and other agents.

Assessment of Therapy

The effects of ex vivo or in vivo therapy according to the methods of the invention can be monitored in a variety of ways. Generally, a sample of blood from the subject can be assayed for, for example, levels of glucose, proinsulin, c-peptide, and insulin. Appropriate assays for detecting proinsulin, c-peptide, insulin and glucose in blood samples are well known in the art. Evidence for recurrent autoimmunity can be gauged by assaying for autoreactive T cells or for antibodies against islet proteins such as glutamic acid decarboxylase (GAD), or other autoantigens well known in the art.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for Unless indicated otherwise, parts are parts by weight, molecular weight is weight average molecular weight, temperature is in degrees Centigrade, and pressure is at or near atmospheric.

Example 1

Detection of Ngn3 Expression in Murine Pancreas

Members of the basic helix-loop-helix (bHLH) family of transcription factors regulate growth and differentiation of numerous cell types. Insulin gene expression is activated by a heterodimeric complex of two bHLH proteins: a ubiquitously expressed (class A) protein and a cell-type-specific (class B) partner, NeuroD1/BETA2. NeuroD1/BETA2 is also important for β-cell development. The targeted disruption of the NeuroD1/BETA2 gene in mice leads to a marked reduction of the β-cell mass at birth due to increased apoptosis of islet cells late in fetal development. There is no apparent defect, however, in β-cell formation or insulin gene expression, despite the postulated importance of this factor in β-cell differentiation.

Assuming that this modest phenotype reflected the redundant expression of closely related class B bHLH proteins in the endocrine pancreas, the inventors searched for additional members of the family by reverse transcriptase-polymerase chain reaction (RT-PCR) using degenerate oligonucleotides primers based on conserved amino acid sequences in the bHLH domain of the class B bHLH proteins (Sommer et al. 1996 *Mol. Cell. Neurosci.* 8:221). PCR analysis revealed that pancreatic endocrine cell lines and isolated adult islets not only express NeuroD1, but also several other members of the family of neural class B bHLH genes as well, including Mash1, neuroD2 and 4 and neurogenins (ngn) 1, 2 and 3. This remarkable degree of redundancy could compensate for the loss of NeuroD1/BETA2 in mice. The two most commonly amplified sequences encoded NeuroD4 and Ngn3, but in situ hybridization studies in mouse pancreas showed highest expression of NeuroD1 and Ngn3. These results were confirmed by immunohistochemistry.

Ngn3 is detected earliest at embryonic day 11.5 (e11.5) in the mouse, increases to a maximum at e15.5 and decreases at e18.5, with no staining seen in the adult pancreas. Ngn3 is detected in the nuclei of scattered ductal cells and periductal cells, and there was no co-staining with any of the four islet hormones (insulin, glucagon, somatostatin and pancreatic polypeptide). This temporal and spatial pattern of expression implicated Ngn3 as a marker for islet cell precursors. Nkx6.1, a specific marker for future beta-cells, was expressed in 10–20% of the Ngn3 positive cells, further supporting the use of Ngn3 as a marker for islet cell precursors. The peak of Ngn3 expression at e15.5 also corresponds with the peak of new beta-cell formation in the fetus. Our data supports a model in which Ngn3 acts upstream of NeuroD1/BETA2 and other islet differentiation factors, marking islet cell precursors, but switching off prior to final differentiation.

Example 2

Isolation and Sequencing of a Human Ngn3 Polypeptide-Encoding Polynucleotide

A probe derived from a cloned fragment of the murine Ngn3 gene (Sommer et al., supra) was used to screen a human genomic library. This screen resulted in the isolation of the genomic sequence provided as SEQ ID NO:1 in the sequence listing. Based on mapping of the murine start site using 5' RACE of mouse fetal pancreatic RNA, the transcriptional start site in the human Ngn3-encoding sequence is at nucleotide residue 2643. The coding sequence is between nucleotide residues 3022–3663, with a stop site at 3664–3666. No introns are within the 5' untranslated region (UTR) or the coding sequence of SEQ ID NO:1.

The promoter of Ngn3 is of interest, particularly given that is it exceptionally well-conserved between mouse, rat, and human. Given the role of Ngn3 in pancreatic and islet cell development, the Ngn3 promoter is likely key to determining the number of islet cells in the mature pancreas. The regulatory region corresponding to the human Ngn3 promoter comprises sequences up to approximately 500 bp upstream of the transcription start site within the human Ngn3 promoter (e.g., from about 2144 to the transcriptional start site at 2643). FISH was used to identify the location of Ngn3 on the human chromosome at 10q22.1–22.2.

Example 3

Isolation and Sequencing of a Murine Ngn3 Polypeptide-Encoding Polynucleotide and Promoter The full-length murine Ngn3 sequence and its 5' flanking sequences, which included the murine Ngn3 promoter, were obtained by sequencing a previously obtained mouse genomic DNA fragment (Sommer, et al., supra). The murine Ngn3 sequence is provided in the Sequence Listing as SEQ ID NO:3, with the encoded polypeptide provided as SEQ ID NO:4. The transcriptional start site was determined using the 5' RACE method and confirmed using Rnase protection with RNA from fetal mouse pancreas, and is at nucleotide residue 719; the coding sequence for murine Ngn3 begins at nucleotide residue 1093. The promoter comprises a region approximately 500 bp upstream of the transcription start site.

Example 4

Construction of Adenovirus Vector Encoding Neurogenin3.

The full length mouse neurogenin3 coding sequence was inserted downstream of the cytomegalovirus immediate early gene promoter (PCMV IE) in the Adeno-X viral genome, and intact viral particles were produced as per the instructions of the manufacturer (Clontech, Palo Alto, Calif.) for the Adeno-XTM Expression System. FIG. 1 provides a map of the final Adeno-X.NGN3 construct. A control construct was produced using a lac Z coding sequence in lieu of Ngn3 to produce an Adeno.LacZ construct. Large scale preparation of adenovirus for the experiments below was performed using protocols well known in the art. Virus concentration was estimated based on the protein concentration of the purified virus stock, not by plaque assay. Identity of the virus was confirmed by PCR during preparation, and by Western blot for neurogenin3 using lysates from cells infected with the purified stock.

Example 5

Induction of Insulin in Normal Adult Rats by Treatment with Adeno-X.NGN3.

Adult male Sprague-Dawley rats weighing 250–350 g were injected with either Adeno.LacZ or Adeno-X.NGN3 into the pancreatic duct using the previously described surgical technique, (Goldfine et al. *Nat Biotechnol* 15:1378–82, 1997). Approximately, $3 \times 10^{10}$ viral particles (low dose) or high dose, $3 \times 10^{11}$ (high dose were injected into the pancreatic duct of each animal. After recovery from the surgery, the animals were returned to a normal diet. After approximately 48 hours, the animals subjected to the low dosage of Adeno-X.NGN3 were sacrificed, the pancreases were removed, fixed, embedded in paraffin and sectioned. The pancreatic sections were stained for insulin, glucagon, cytokerratin20 (a marker for ducts), and mouse neurogenin3 using established immunohistochemical techniques and antisera (Schwitzgebel et al. *Development* 127:3533–3542, 2000.).

Figure 2A:
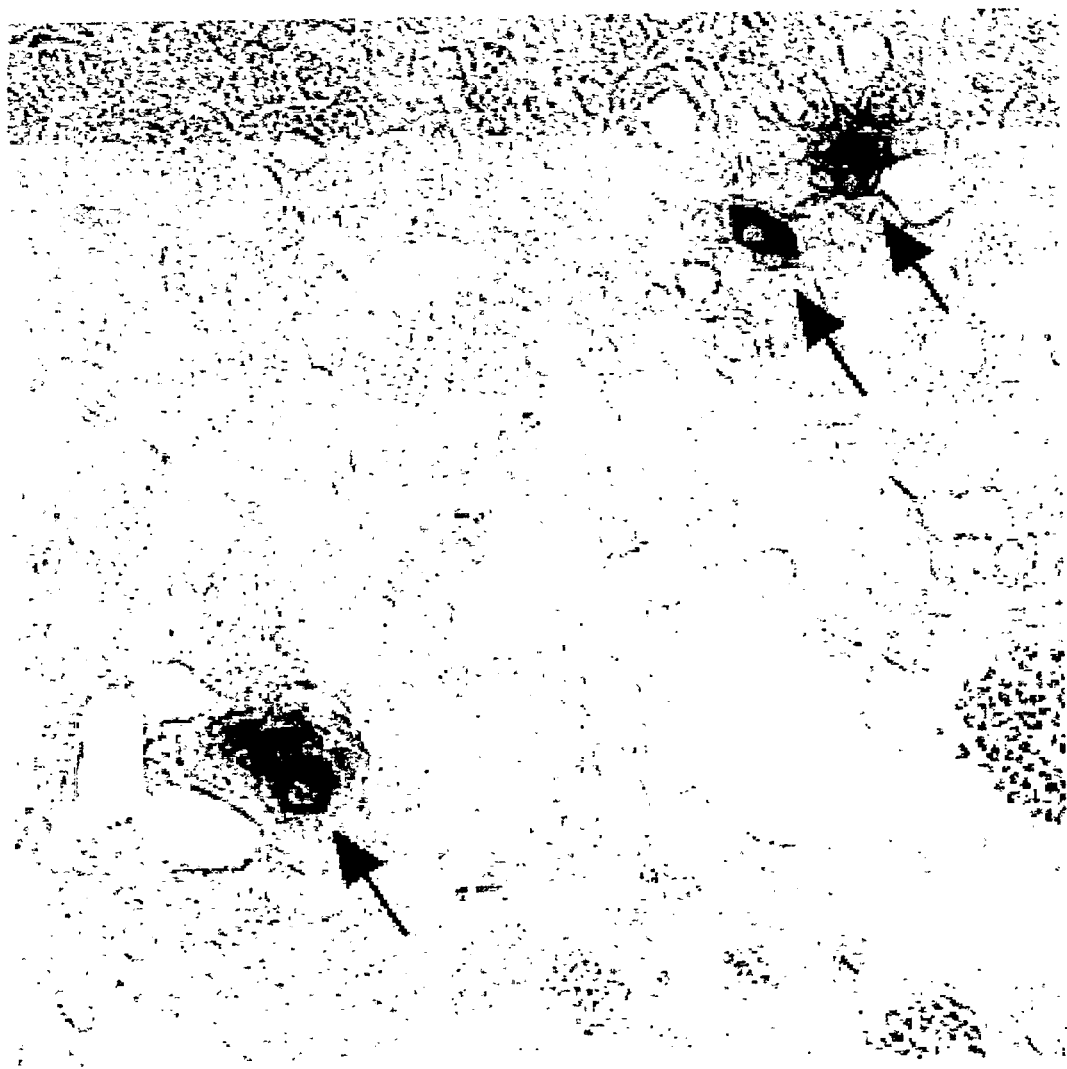
FIG. 2A is a photograph showing histological staining for insulin in a pancreatic tissue section of an animal injected with Adeno-X.NGN3 at high magnification (40×) which indicates the production of insulin in accordance with the invention. The arrows indicate insulin staining cells.
Figure 2B:
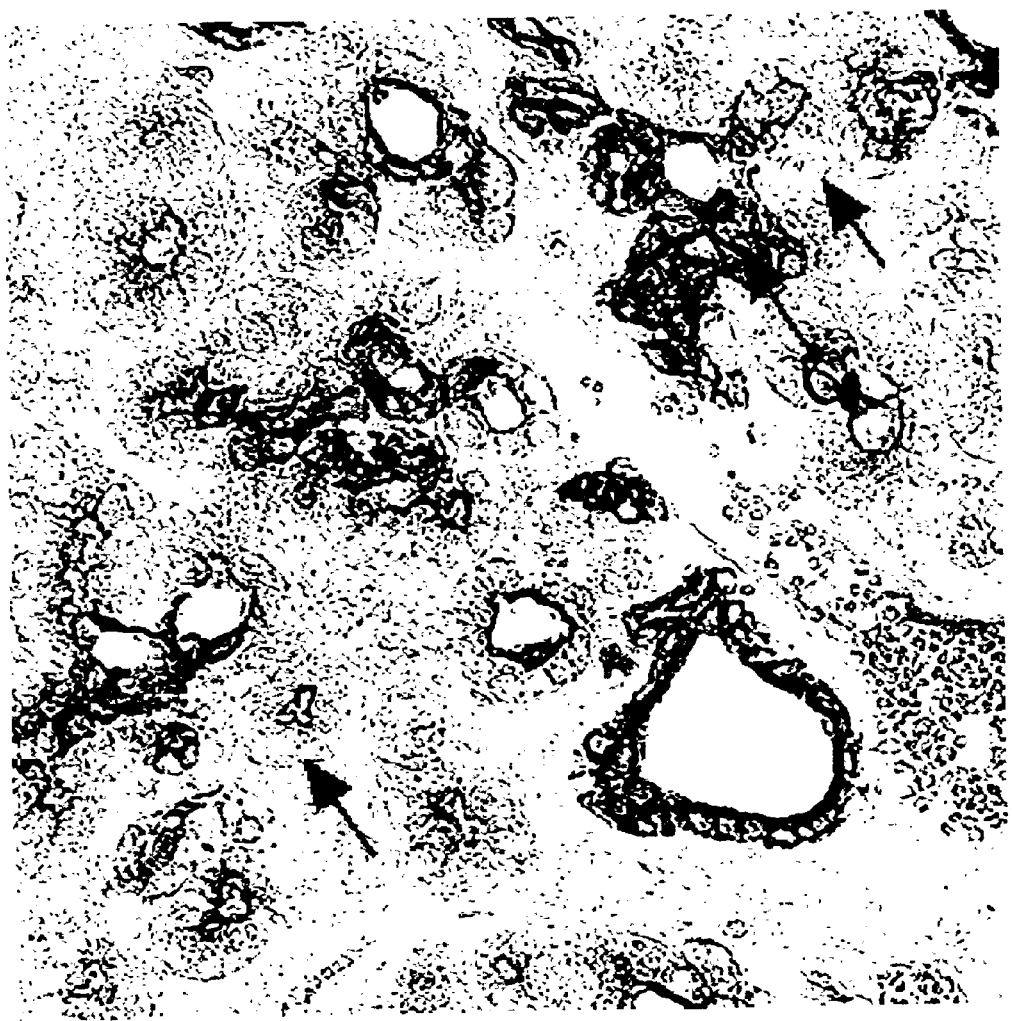
FIG. 2B is a photograph of a serial section of FIG. 3A, stained for the duct cell marker cytokeratin20. The arrows indicate the position of insulin staining cells in the serial sections.

Animals injected with the low or high dose of Adeno-X.NGN3 had individual or small clumps of 8 or fewer insulin or glucagon staining cells found scattered near the ducts, in addition to the normal large (approximately 1000 cells) aggregations of glucagon and insulin staining cells that form the islets of Langerhans. FIG. 2A shows the results of histological staining for insulin in a pancreatic tissue section of an animal injected with low dose ($3 \times 10^{10}$) Adeno-X.NGN3. Individual and small clumps of insulin staining cells are indicated with arrows. FIG. 2B shows a serial section from the same animal stained for the duct cell marker cytokeratin 20, with the arrows indicating the position of the insulin staining in FIG. 2A.

Animals injected with the control Adeno.LacZ virus had no scattered insulin or glucagon staining cells outside of the islets of Langerhans. All of the animals injected with high titer of the neurogenin3 expressing adenovirus died within 36 hours after injection. One of the high dose animals before death had a blood glucose level of 32 mg/ml measured by the glucose oxidase method using the Glucometer Elite meter (Bayer Corporation, Elkhart, Ind.). The blood glucose level for fasted rat is normally approximately 100 mg/dl and rarely seen below 70 mg/dl. The blood glucose level of 32 mg/ml for the high dose animal indicates that excess insulin was being produced to lower the blood glucose to hypoglycemic levels. The animals injected with the high dose of DNA encoding Ngn3 appeared to have died from hypoglycemia induced by the overexpression of insulin from the newly produced β cells.

Figure 3:
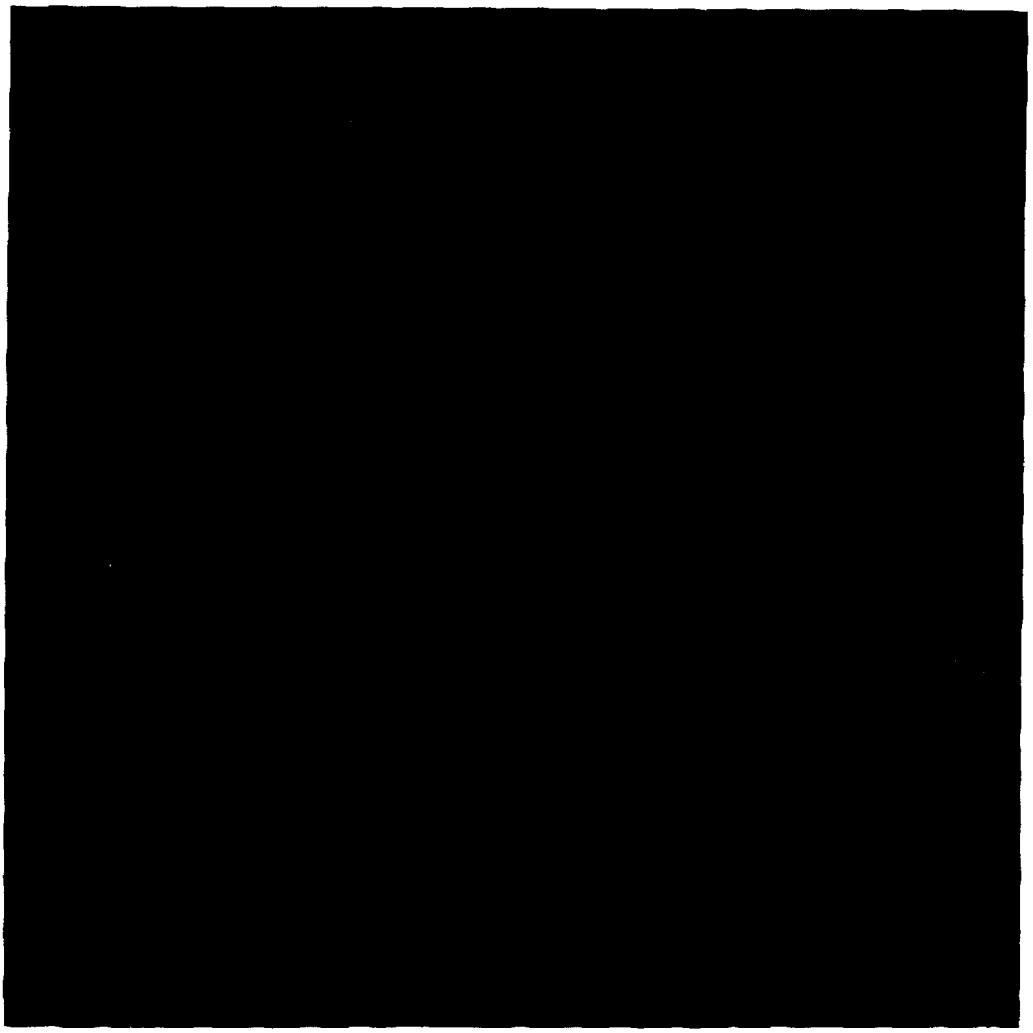
FIG. 3 is a photograph of a confocal image with fluorescent co-staining for insulin in red and neurogenin3 in green in the pancreas of an animal injected with Adeno-XZ.NGN3. The production of neurogenin3 and insulin can be detected in the same cell in accordance with the invention.

FIG. 3 shows a confocal image with fluorescent co-staining for insulin in red and neurogenein3 in green in the pancreas of an animal infected with high dose ($3\times10^{11}$) Adeno-X.NGN3 and harvested at approximately 24 hours. It can be seen that the cell in the center of the figure stains for insulin in the cytoplasm and neurogenin3 in the nucleus. No neurogenin3 could be detected in the pancreases of the control animals.

Example 6

Normalization of Blood Glucose Levels in Diabetic Induced Adult Rats Induced by the Introduction of DNA Encoding Murine Ngn3 into the Pancreas Diabetes was induced in adult male Sprague-Dawley rats weighing 250–350 g by injection with the beta-cell toxin of streptozotocin (Sigma: 40 mg/kg of body weight, in 1 mM citrate buffer, pH 4.5) into the peritoneal space on day 1 and day 2. Streptozotocin is a β-cell toxin which induces diabetes mellitus in rats. On day 4, animals that were confirmed to have hyperglycemia (blood glucose greater than 300 mg/dl measured by the glucose oxidase method using the Glucometer Elite meter (Bayer Corporation, Elkhart, Ind.) were injected with either Adeno.LacZ or Adeno-X.NGN3 into the pancreatic duct using the previously described surgical technique. Approximately, $3\times10^{10}$ or $3\times10^{11}$ viral particles were injected into the pancreatic duct of each animal.

Figure 4A:
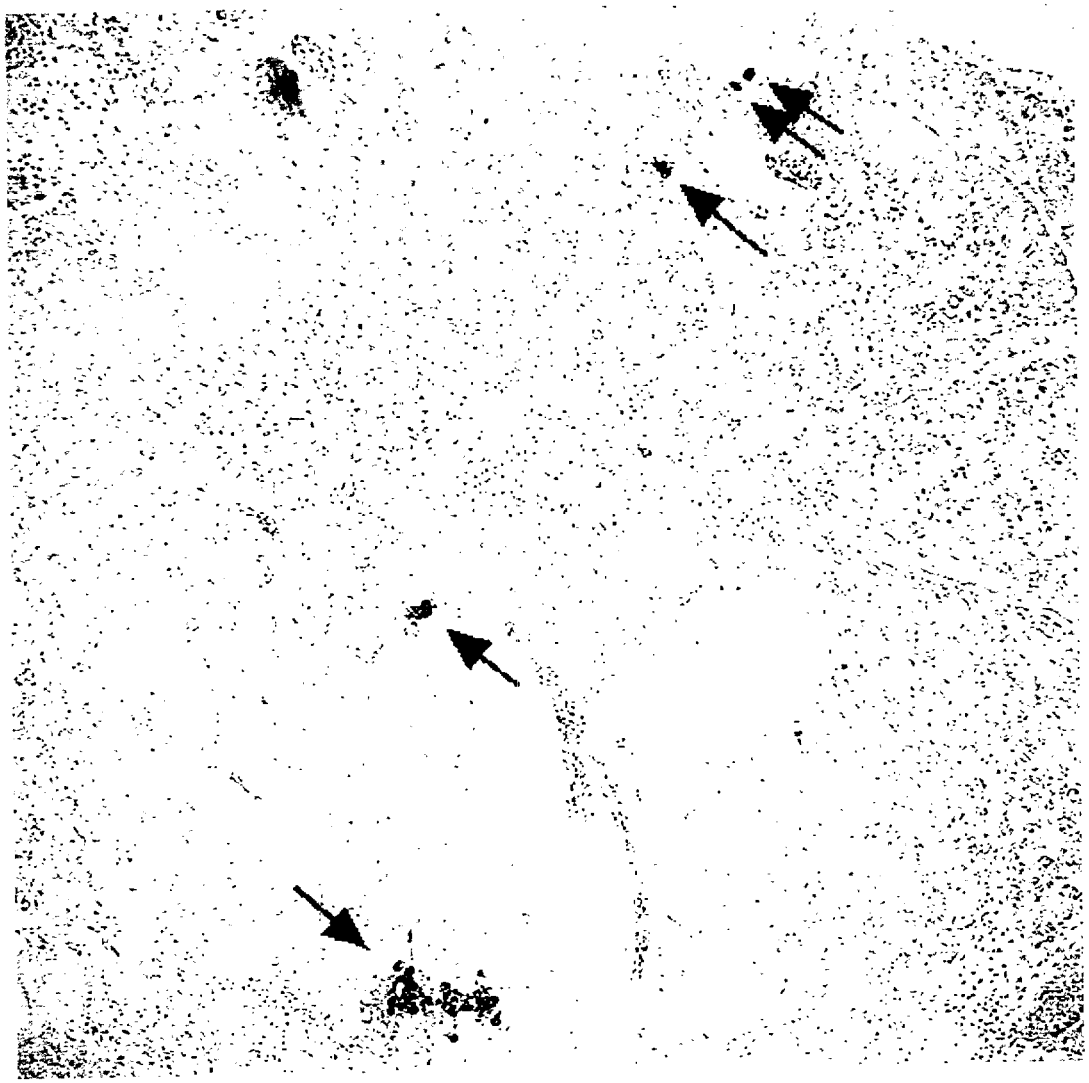
FIG. 4A is a photograph showing histological staining for insulin in a pancreatic tissue section of an animal made diabetic with streptozotocin and injected with Adeno-X.NGN3 indicating the production of insulin producing cells in accordance with the present invention. Red arrows indicate individual and small clusters of insulin staining cells. Black arrows indicate residual and degenerating cells remaining in formed islets after streptozotocin treatment.

Five days after surgery, the animals were sacrificed, the pancreases were removed, fixed, embedded in paraffin and sectioned. The pancreatic sections were stained for insulin, glucagon, cytokeratin 20 (a marker for ducts), and mouse neurogenin3. FIG. 4A shows the results of histological staining for insulin in a pancreatic tissue section of an animal injected with Adeno-X.NGN3 which indicates the production of insulin in accordance of the invention. Individual and small clumps of insulin staining cells are indicated with red arrows. An islet with a few residual insulin staining cells (the remainder having been destroyed by streptozotocin) is indicated with a black arrow.

Figure 4B:
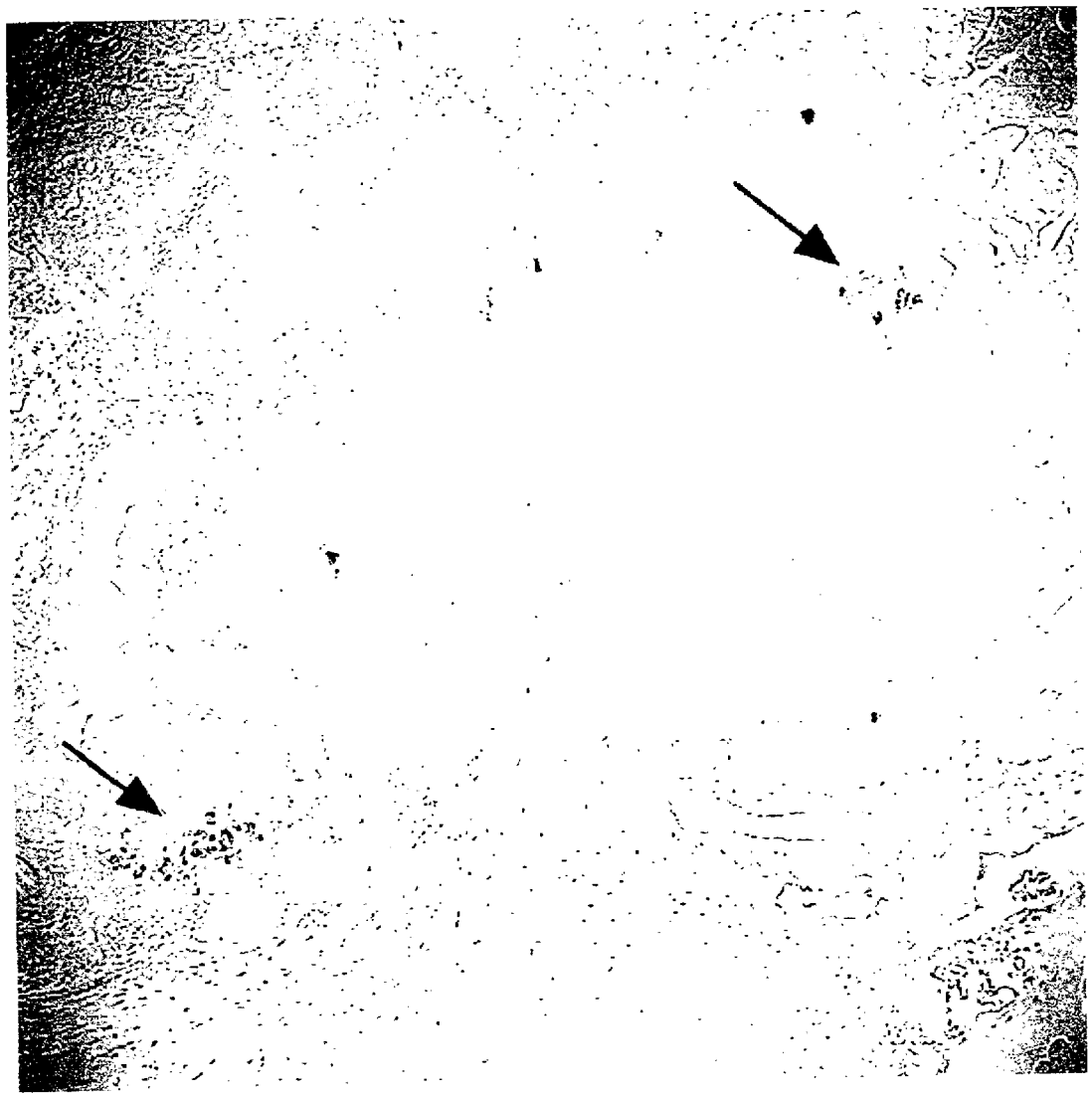
FIG. 4B is a photograph showing staining for insulin in a pancreatic tissue section of an animal injected with Adeno.LacZ, a control viral construct. Black arrows indicate residual and degenerating cells remaining in formed islets after streptozotocin treatment. Note individual and small clusters of insulin staining cells are seen.

FIG. 4B shows the results of staining for insulin in the pancreas of an animal injected with Adeno-LacZ virus. Two islets with a few residual insulin staining cells are indicated with black arrows. No individual or small clumps of insulin staining cells were detected in the control animals.

Figure 5:
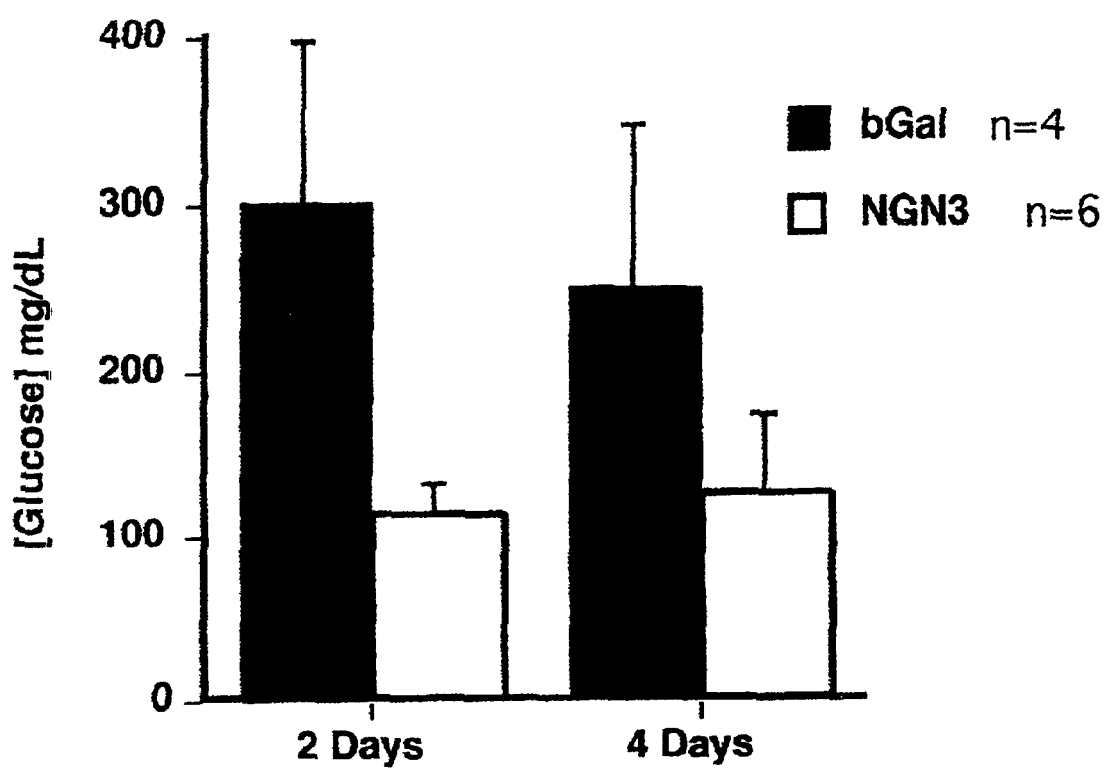
FIG. 5 is a graphical illustration of blood glucose levels of streptozotocin-treated animals (diabetic) that received either AdenoX-.NGN3 or Adeno.LacZ (control animals).

The animals injected with the Adeno-X.NGN3 virus had significantly lower blood glucose levels than the control animals injected with Adeno.LacZ. As shown in FIG. 5, blood glucose levels were significantly decreased in the diabetic rats that received AdenoX-.NGN3 relative to the diabetic rats that received Adeno.LacZ. The decreased blood glucose levels were observed on both day 2 and day 4. Thus, these data show that introduction of Ngn3-encoding DNA into the pancreas results in persistent expression of insulin, and that the insulin expressed by the transformed pancreatic cells is secreted into the bloodstream and can function in regulation of blood glucose at levels sufficient to overcome diabetes in an animal model.

The present invention demonstrates that cells in the mature pancreas, most likely duct cells, retain the capacity to differentiate into endocrine cells. Adult duct cells respond to pro-endocrine bHLH genes, and in particular, Ngn3, and in combination with other signals these genes can induce new beta cell formation and subsequent insulin production. The present invention will be useful in the maintenance and treatment of type 2 diabetes and also allow for the replacement of beta cells lost to autoimmune destruction in individuals with type 1 diabetes.

Example 7

Overexpression of Ngn3 and Islet Cell Production in Ngn3 Transgenic Animals

As previously described (Schwitzgebel et al *Development* 127:3533–3542, 2000), the pdx1 promoter vector pBAT.PD17 was constructed by inserting the mouse pdx1 promoter (a 4.4 kb XbaI-Sma I fragment from the mouse Pdx1 gene containing the transcription start site and promoter (Apelqvist et al. *Curr Biol* 7:801–804; Wu et al. *Mol Cell Biol* 17:6002–6013 (1997)), and the human beta-globin gene first intron upstream of the pBAT polylinker (German et al. *Genes & Dev* 6:2165–2176), and the SV40 late gene polyadenylation signal. A 663 bp DNA fragment encoding full length mouse ngn3 cDNA was obtained by PCR from the mouse genomic neurogenin3 clone (Sommer et al. *Mol Cell Neurosci* 8:221–241 (1996)) and inserted into the pBAT.PD17 polylinker.

The vectors were linearized and purified, and transgenic mice were generated by pronuclear injection (1.5 ng/μl) into F1 hybrid oocytes from C3Fe/B6 parents (Hogan et al. (1994) Manipulating the mouse embryo: A Laboratory Manual. New York: Cold Spring Harbour Laboratory Press.). Genotypes were determined by PCR analysis of genomic DNA from tail biopsies. The primers used were: 5' TGGAGAACTGTCAAAGCGATCTG (SEQ ID NO:5) (Pdx1-primer for 5') and 5' CACATGCCCAGTTTCTATTGGTC (SEQ ID NO:6) (human beta-globin intron for 3').

Figure 7A:
FIG. 7 is a photograph showing the gut and associated organs embryonic day 18.5 for fetal mice over-expressing (a) ngn3 or (B) neuroD1 under the control of the pdx1 promoter. Non-transgenic littermates are shown at the right in each panel. Arrows point towards the following organs: liver (L), stomach (St), spleen (sp), and pancreas (P). Reduced pancreatic tissue is not visible in the transgenic animals.

Embryos were harvested at embryonic day 12.5 (E12.5) or E18.5. A total of 6 pdx1-ngn3 animals were examined at E12.5, and 10 at E18.5. The transgenic embryos were not grossly abnormal in size. Transgenic embryos harvested at E12.5 have an increase in the numbers of islet cells as indicated in FIG. 6B by staining for glucagon. The control, non-transgenic embryos have normal numbers of glucagon expressing cells (FIG. 6A). At E18.5, the pancreas size is grossly reduced in the transgenic animals, but the fraction of islet cells is markedly increased relative to the same age control animals (FIG. 7A).

These experiments demonstrate that neurogenin3 is capable of inducing islet cell neogenesis in appropriate progenitor cells.

Example 8

Islet Cell Production in NeuroD1 Transgenic Animals

The neuroD1/BETA2 vector was constructed by cloning into pBAT.PD17 a 1.7 Kb DNA fragment encoding the full length mouse cDNA (Lee et al. (1995) Science 268:836–844) extending from the start codon through the 3' UTR.

The vectors were linearized and purified, and transgenic mice were generated by pronuclear injection (1.5 ng/µl) into F1 hybrid oocytes from C3Fe/B6 parents as described (Hogan et al. (1994), supra). Genotypes were determined by PCR analysis of genomic DNA from tail biopsies. The primers used were: 5' TGGAGAACTGTCAAAGC-GATCTG (SEQ ID NO:5) (Pdx1-primer for 5') and 5' CACATGCCCAGTTTCTATTGGTC (SEQ ID NO:6) (human beta-globin intron for 3').

Figure 7B:
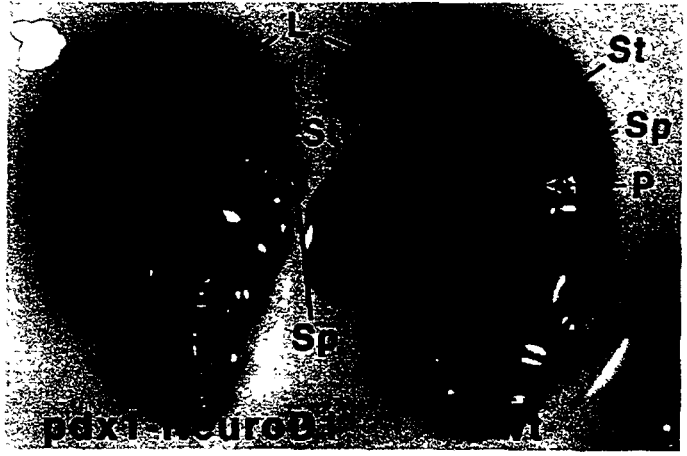

Embryos were harvested at embryonic day 12.5 (E12.5) or E18.5. A total of 5 pdx1-neuroD1 animals were examined at E12.5, and 10 at E18.5. Similar to the neurogenin3 transgenic animals, the pdx1-neuroD1 transgenic embryos harvested at E12.5 have an increase in the numbers of islet cells as indicated in FIG. 6C by staining for glucagon. At E18.5, the pancreas size is grossly reduced in the transgenic animals, but the fraction of islet cells is markedly increased relative to the same age control animals (FIG. 7B).

These experiments demonstrate that like neurogenin3, neuroD1 is capable of inducing islet cell neogenesis in appropriate progenitor cells.

Example 9

Construction of Adenovirus Vector Encoding NeuroD1

The full-length mouse or human neuroD1 coding sequence is inserted downstream of the cytomegalovirus immediate early gene promote (PCMV IE) in the adenoviral genome, and intact viral particle produced according to methods well known in the art, for example as per the instructions of the manufacturer (Clontech, Palo Alto, Calif.), for the Adeno-XTM Expression System. FIG. 8 provide a map of such an exemplary Adeno-NeuroD1 construct.

Example 10

Construction of Adenovirus Vector Encoding Mash1/ASCL1/ASH1

The full length mouse mash1 or human ACSL1/ASH1 (human symbols for mas1) coding sequence are inserted downstream of the CMV immediate early gene promoter (PCMV IE) in the adenoviral genome, and intact viral particle produced according to methods well known in the art, for example as per the instructions of the manufacturer (Clontech, Palo Alto, Calif.), for the Adeno-XTM Expression System. FIG. 8 is a map of such an exemplary Adeno-mash1/ASCL1/ASH1 construct.

Example 11

Induction of the Formation of Insulin-producing Beta-cells in Normal Adult Rats by Treatment with Adeno-NEURD1

Adult male Sprague-Dawley rats weighing 250–350 g are injected with either Adeno.LacZ or Adeno-neuroD1 (mouse or human) into the pancreatic duct using previously described surgical techniques (see, e.g., Goldfine, et al. *Nat. Biotechnol* 15:1378–82 (1997)). Approximately $3\times10^{10}$ viral particles (low dose) or $3\times10^{11}$ (high dose) are injected into the pancreatic duct of each animal. After recovery from the surgery, the animal are returned to normal diet. After approximately 48 hours, the animals are sacrificed, the pancreases removed, fixed, embedded n paraffin, and sectioned. The pancreatic sections are stained for insulin, glucagons, cytokerratin20 (a marker for ducts), and neuroD1 using established immunohistochemical techniques and antisera (Schwitzgebel, et al. *Development* 127:3533–3542, 2000).

Example 12

Induction of the Formation of Insulin-producing Beta-cells in Normal Adult Rats by Treatment with Adeno-mash1/ASCL1/ASH1.

Adult male Sprague-Dawley rats weighing 250–350 g are injected with either Adeno.LacZ or Adeno-mash1/ASCL1/ASH1 (mouse or human) into the pancreatic duct using previously described surgical techniques (see, e.g., Goldfine, et al. *Nat. Biotechnol* 15:1378–82 (1997)). Approximately $3\times10^{10}$ viral particles (low dose) or $3\times10^{11}$ (high dose) are injected into the pancreatic duct of each animal. After recovery from the surgery, the animal are returned to normal diet. After approximately 48 hours, the animals are sacrificed, the pancreases removed, fixed, embedded n paraffin, and sectioned. The pancreatic sections are stained for insulin, glucagons, cytokerratin20 (a marker for ducts), and neuroD1 using established immunohistochemical techniques and antisera (Schwitzgebel, et al *Development* 127:3533–3542, 2000).

Example 13

Production of Insulin in Diabetic Induced Adult Rats by the Introduction of DNA Encoding NeuroD1 into the Pancreas Diabetes is induced in adult male Sprague-Dawley rats weighing 250–350 g by injection with the beta-cell toxin streptozotocin (Sigma: 40 mg/kg of body weight, in 1 mM citrate buffer, pH 4.5) into the peritoneal space on day 1 and day 2. Streptozotocin is a beta-cell toxin which induces diabetes mellitus in rats. On day 4, animals confirmed to have hyperglycemia (blood glucose greater than 300 mg/dl measured by the glucose oxidase method using the Glucometer Elite meter (Bayer Corporation, Elkhart, Ind.) are injected with either Adeno-LacZ or Adeno-NEUROD1 (mouse or human) into the pancreatic duct using the previously described surgical technique. Approximately $3\times10^{10}$ or $3\times10^{11}$ viral particles are injected into the pancreatic duct of each animal. Animals would then be monitored every 12 hours for a fall in blood glucose levels.

Example 14

Production of Insulin in Diabetic Induced Adult Rats by the Introduction of DNA Encoding Mash1/ASCL1/ASH1 into the Pancreas Diabetes is induced in adult male Sprague-Dawley rats weighing 250–350 g by injection with the beta-cell toxin streptozotocin (Sigma: 40 mg/kg of body weight, in 1 mM citrate buffer, pH 4.5) into the peritoneal space on day 1 and day 2. Streptozotocin is a beta-cell toxin which induces diabetes mellitus in rats. On day 4, animals confirmed to have hyperglycemia (blood glucose greater than 300 mg/dl measured by the glucose oxidase method using the Glucometer Elite meter (Bayer Corporation, Elkhart, Ind.) are injected with either Adeno-LacZ or Adeno-mash1/ASCL1/ASH1 (mouse or human) into the pancreatic duct using the

Example 15

Construction of Plasmid Vector Encoding Neurogenin3

Figure 9:
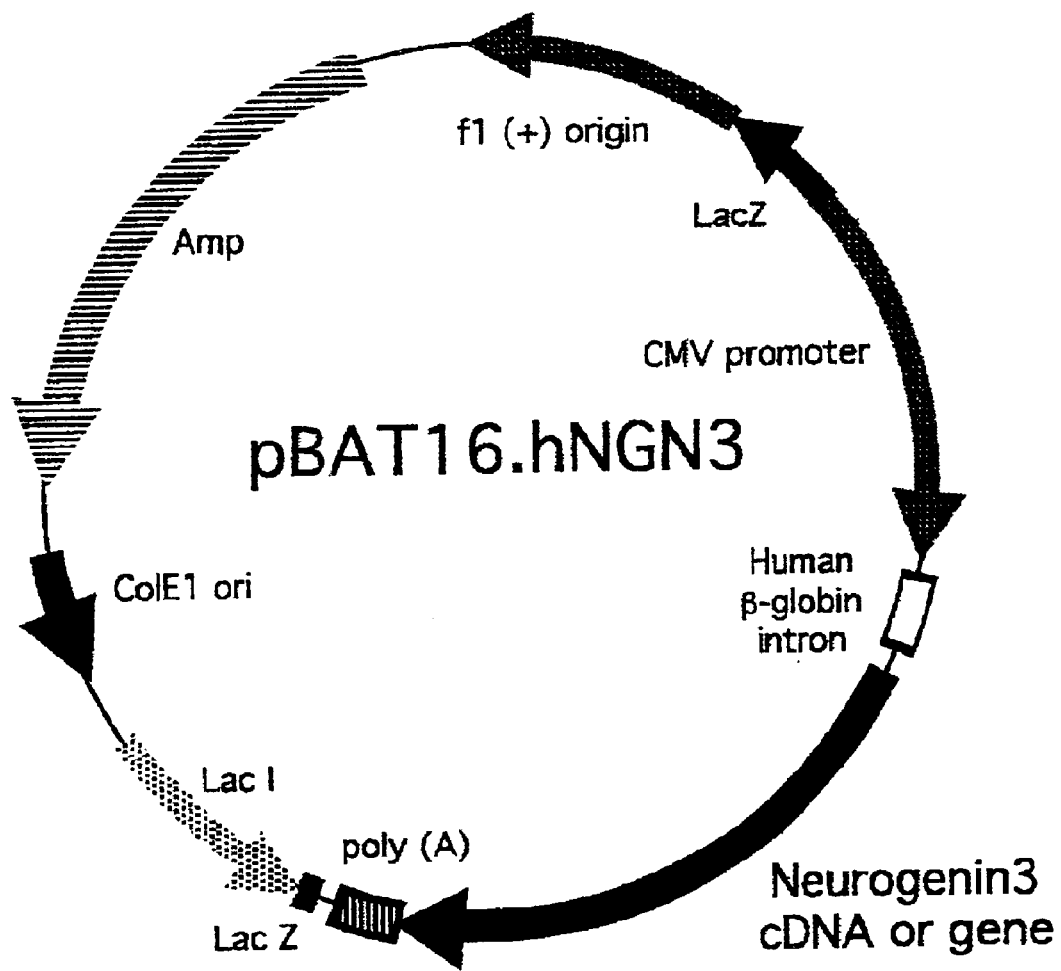
FIG. 9 is a map of the pBAT16.NGN3 plasmid DNA construct, which contains the neurogenein3 sequence operably linked to the CMV promoter.

The full length mouse or human neurogenin3 coding sequence, either cDNA or gene is inserted downstream of the CMV immediate early gene promoter (PCMV IE) and the human beta-globin gene intron, and upstream of the SV40 polyadenylation signal in the pBAT16 plasmid vector, which also contains the colE1 origin of replication for high copy number replication in bacteria, and the bacterial ampicillin resistance gene for selection of plasmid-containing bacteria. Purified plasmid DNA is produced according to methods well known in the art. FIG. 9 provides a map of such an exemplary pBAT16.hNGN3 construct.

Example 16

Production of Insulin in Diabetic Induced Adult Rats by the Introduction of Plasmid DNA Vector pBAT16.hNGN3 into the Pancreas Diabetes is induced in adult male Sprague-Dawley rats weighing 250–350 g by injection with the beta-cell toxin streptozotocin (Sigma: 40 mg/kg of body weight, in 1 mM citrate buffer, pH 4.5) into the peritoneal space on day 1 and day 2. Streptozotocin is a beta-cell toxin which induces diabetes mellitus in rats. On day 4, animals confirmed to have hyperglycemia (blood glucose greater than 300 mg/dl measured by the glucose oxidase method using the Glucometer Elite meter (Bayer Corporation, Elkhart, Ind.) are injected with either Adeno-LacZ or Adeno-mash1/ASCL1/ASH1 (mouse or human) into the pancreatic duct. The ability of naked DNA, with or without adjuvants such as cationic lipids, to express genes in pancreatic cells when injected into the pancreatic duct has been described previously (Goldfine et al 1997, supra). In a similar manner, 8–25 µg of the plasmid DNA is injected into a lumen of the pancreatic duct with or without adjuvant such as the cationic lipid reagent Transfast (Promega). Animals are then monitored every 12 hours for a fall in blood glucose levels.

Example 17

Production of Insulin in Mice with Autoimmune Diabetes by the Introduction of AdenoX-NGN3 or Plasmid DNA Vector pBAT16.hNGN3 into the Pancreas The NOD mouse develops a form of autoimmune diabetes that is an accepted model for human autoimmune, or "type 1" diabetes mellitus (for a review, see, e.g., Bach et al. The NOD mouse. Research in Immunology, 1997 June, 148(5):285–6). These animals have been used as a model for testing in an autoimmune setting treatment for diabetes, such as islet transplantation (for reviews see, e.g., Hahn et al. *Adv. Exp. Med Biol.* 1997 426:411–9; Sutherland *Transplantation Proc.* 1996, 28(4):2131–3).

In this example, adult mice greater than 15 weeks of age are tested for diabetes (blood glucose greater than 300 mg/dl measured by the glucose oxidase method using the Glucometer Elite meter (Bayer Corporation, Elkhart, Ind.) are injected with either Adeno-LacZ or AdenoX-NGN3 (mouse or human) into the pancreatic duct using the previously described surgical technique. Approximately $3 \times 10^9$ or $3 \times 10^{10}$ viral particles are injected into the pancreatic duct of each animal, or 2–25 µg of plasmid DNA. Animals are monitored every 12 hours for a fall in blood glucose levels.

To prevent recurrence of autoimmunity and destruction of the newly formed beta-cells, several methods are well known in the art, including, but not limited to, the use of drugs that suppress the immune system, such as cytoxan or FK506, or reagents that block co-stimulatory molecules such as antibodies to CTLA-4 (Shapiro et al. *New Engl. J. Med.* 2000 343(4):230–8; Griffin et al. *J. Immunol,* 2000 164(9):4433–42). Animals are treated with the anti-autoimmune therapy starting 2 days prior to DNA injection, and maintained on the immunotherapy throughout the experiment.

Example 18

Induction of the Formation of Islet Cell in vitro

In this example, neurogenin3 is used to induce islet cell formation form non-islet cells cultured in vitro. The cells used can include, but would not necessarily be limited to, immortalised mammalian cell lines, or primary cultured mammalian cells including cells from the gastrointestinal organs such as pancreatic duct cells, pancreatic acinar cells, gut cells including crypt cells, liver cells, and salivary gland cells; adult stem cells such as hematopoietic stem cells, neural stem cells, muscle stem cells or pancreatic stem cells or embryonic stem cells. Cells are cultured using methods well known in the art. Neurogenin3 is introduced by viral vector (such as with the AdenoXZ-NGN3 vector) or naked DNA using a DNA plasmid vector such as pBAT16.hNGN3 along with adjuvant such as the cationic lipid transfection reagent Transfast. Cells are continued in culture for a period ranging from one day to several weeks. Detection of newly formed islet cells is performed by measuring for islet hormones such as insulin or glucagons with radio immune assays or ELISA in an extract made from a sample of the cells, or by measuring hormone levels in the culture media using methods well known in the art.

Example 19

Delivery of Ngn3-Encoding Nucleic Acid to a Human Subject

In this example, patients with diabetes mellitus or a relative deficiency of insulin are treated with neurogenin3 encoding DNA with the purpose of inducing new islet cell formation. The neurogenin3 encoding DNA can be contained in a viral vector, as in the AdenoX-NGN3 example above, or in a naked DNA vector, as in the pBAT16.NGN3 example above with or without an adjuvant such as the cationic lipid Transfast. The vector is introduced into the pancreas retrograde through the pancreatic duct. In the example where the vector is an adenovirus, the amount injected is determined by the amount needed to lower the blood glucose and maintain it in a normal range, may be approximately about $10^{11}$ to about $10^{14}$ viral particles. Where the vector is a naked DNA vector, the amount required may be from about 100 µg to 100 mg of DNA.

To prevent recurrence of autoimmunity and destruction of the newly formed beta-cells, several methods are well known in the art, and have been used clinically in humans, including, but not limited to, the use of drugs that suppress the immune system, such as cytoxan, FK506, or sirolimus;

or reagents that block co-stimulatory molecules such as antibodies to CTLA-4 (Shapiro et al *New Engl. J. Med.* 2000 343(4):230–8; Griffin et al. *J. Immunol,* 2000 164(9):4433–42). Patients are treated with the anti-autoimmune therapy starting 1–2 days prior to DNA administration, and maintained on the immunotherapy afterwards.

After the procedure, the blood glucose is monitored closely, as often as hourly, or by use of a continuous glucose monitor, and insulin therapy by subcutaneous injection decreased or stopped as needed. If blood glucose does not completely normalize without exogenous insulin, the procedure is repeated. To monitor for recurrent autoimmune destruction of the new beta-cells, the blood glucose is monitored periodically. In addition direct evidence of an immune response to new cells can be tested by assaying for autoreactive T cells, antibodies to glutamic acid decarboxylase (anti-GAD antibodies) or to islet antigens (islet cell antibodies or ICA). Evidence of recurrent autoimmunity can be treated with an increase or other change in the immunosuppression therapy.

Example 20

Characterization of and Regulation of the Neurogenin3 Promoter

The following experiments provide for characterization of the Ngn3 promoter, as well as identification of factors both upstream and downstream of Ngn3 that participate in the regulatory pathway that controls Ngn3 expression.

Materials and Methods

The following materials and methods were used in the present example.

Cloning of the Mouse and Human ngn3 Gene Promoter. A lambda phage genomic clone containing the mouse neurogenin 3 open reading frame, clone 17/6-1-1-2 (Sommer et al. *Mol. Cell. Neurosci.* 8:221–241, 1996). From this phage clone, a 1 kb fragment containing sequences upstream of the open reading frame was subcloned and sequenced. Human neurogenin 3 genomic clones were obtained by screening a lambda DASH human genomic library with the mouse neurogenin 3 genomic fragment. The clone containing the longest 5' flanking sequence, clone 14H, was subcloned, sequenced, and used for generating reporter gene plasmids.

5' Rapid amplification of cDNA ends (RACE). The 5' end of the mouse ngn3 cDNA was identified by 5'-RACE, using a modification of the protocol from the 5'-RACE System Version 2.0 (GibcoBRL). For mouse cDNA, 2.5 pmol of specific primer JL1 (5'-ATCCTGCGGTTGGGAA-3' (SEQ ID NO:7)) was annealed to 1 µg of total RNA from mouse E15.5 pancreas. Reverse transcription was carried out using SuperScript II reverse transcriptase (GibcoBRL). After first strand cDNA synthesis, the original mRNA template was removed by treatment with RNase and homopolymeric dCTP tails was then added to the 3'-end of the CDNA using terminal deoxynucleotidyl transferase. Using this products as a template, we carried out 35 cycles of PCR using the 5' RACE Abridged Anchor Primer (Gibco BRL) and JL2 (5'-TGGAAGGTGTGTGTGTGCCAG-3' (SEQ ID NO:8)) as primers. For the nested PCR, we used Abridged Universal Amplification Primer (Gibco BRL) and JL3 (5'-GATCTAGAGACTTAGAGGTCACTGC-3' (SEQ ID NO:9)) as primers, and performed 35 cycles of PCR. The PCR products were subcloned and sequenced.

Reporter gene constructs. To generate reporter plasmids, fragments of the 5' region of the human ngn3 gene obtained by restriction digestion were ligated upstream of the luciferase gene in the plasmid pFOXLuc1 or upstream of the TK minimal promoter gene in the plasmid pFOXLuc1TK (Mirmira et al *J. Biol Chem* 275:14743–51, 2000).

Cell culture and transient transfections. βTC3 cells, αTC1.6, and MPAC cells were grown in Dulbecco's Modified Eagle Medium (DMEM) supplemented with 2.5% fetal bovine serum and 15% horse serum. NIH3T3 cells were grown in DMEM medium supplemented with 10% calf serum. Cos7 cells were grown in DMEM medium with 10% fetal bovine serum with 4 mM glutamine. For transient mammalian cell transfections, cells were plated in six-well tissue culture plates 24 h before transfection. For the standard reporter gene analysis, 2 µg of luciferase reporter plasmids were transfected into the cells using TRANSFAST lipid reagent (Promega) according to the manufacturers instructions. For assessing the effect of the expression of HES1 on the ngn3 promoter, we cotransfected the amount of HES1, or dominant negative Hes1 (pcDNA3Hes1 (kind1 y provided by R. Kageyama, Kyoto University (Sasai et al. *Genes Develop.* 6:2620–2634, 1992) expression plasmid DNA indicated with 2 µg of luciferase reporter plasmids. Forty-eight hours after transfection, cells were harvested and luciferase assays were performed as described previously (German et al *Genes & Dev.* 6:2165–2176, 1992). Luciferase activity was corrected for cellular protein concentration. All reporter gene analyses were performed on at least three occasions and data are expressed as mean±SEM.

Generation of transgenic mouse and detection of β-galactosidase. The plasmids pNAT6B and pNAT3B were generated by ligating human ngn3 promoter fragments extending from −5.7 kb to +261 bp and from −2.6 kb to +261 bp upstream of the human β-globin intron and the bacterial β-galactosidase gene. Each plasmid was linearized and microinjected (1.5 ng/µl) into murine pronuclei. The injected embryos were transferred to pseudopregnant females and the fetal pancreata with stomach and small intestine were harvested at e15.5 from the founder mice. Tissues were prefixed for 30 minutes at 4° C. in 4% paraformaldehyde, and then incubated overnight in X-gal (400 µg/ml) substrate at 37° C. (−2.6 kb promoter) or room temperature (−5.7 kb promoter). Tissues were then fixed again in 4% paraformaldehyde for 30 minutes, paraffin embedded, and sectioned at 5 µM. Genotype was determined by PCR using primers specific for the human ngn3 promoter sequence. β-galactosidase activity was assayed in 6 independent founder fetuses that had integrated the −2.6 kb promoter construct, and in 8 independent founder fetuses that had integrated the −5.7 kb promoter construct.

Immunohistochemistry. Immunohistochemistry was performed on paraffin embedded sections as described previously (Schwitzgebel et al. *Development* 127:3533–3542, 2000.). Primary antibodies were used at the following dilutions: guinea pig anti-insulin (Linco), 1:5000; guinea pig anti-glucagon (Linco), 1:10000; rabbit anti-ngn3 (Schwitzgebel et al. *Development* 127:3533–3542, 2000), 1:5000. Biotinylated secondary antibodies (Vector) were detected with the ABC Elite immunoperoxidase system (Vector).

Preparation of proteins and elecrophoretic mobility shift assay (EMSA). HNF3β and HNF1α proteins were produced in vitro using SP6 and T7 TNT Quick Coupled Lysate System® (Promega) using pGEM-1ratHNF3β (generous gift from R. Costa, University of Illinois at Chicago) and pcDNA3-HNF1α (generous gift from M. Stoffel, Rockefeller University) as templates. Glutathione S-transferase (GST) fused HES1 protein was produced in *Escherichia coli*

BL21 competent cells using the pGEX2T plasmid system (Promega). Nuclear extracts from αTC1.6 cells, βTC3 cells, and NIH3T3 cells were prepared following the procedure described by Sadowski and Gilman (Sadowski and Gilman. *Nature* 362:79–83, 1993).

Single-stranded oligonucleotides corresponding to the sequences in the human ngn3 promoter were 5' end-labeled with [γ-$^{32}$P]-ATP using T4 polynucleotide kinase. The labeled oligonucleotides were column-purified and annealed to an excess of the complementary strand. For HNF3β and HNF1α binding experiments, EMSA buffers and electrophoresis conditions were as previously described (Mirmira et al. *J. Biol Chem* 275:14743–51, 2000). For HES-1 binding experiments, conditions were the same except that the poly(dI-dC) concentration was decreased to 15 ng/μl. One μl of the in vitro reaction mixture or 2 ug of nuclear extracts or 400 ng of GST-fused Hes1 protein were used for each binding reaction. When using antibodies, 1 μl of each antibody was incubated with the binding mix for 15 min at room temperature prior to gel-electrophoresis. The antisera against HNF-3α, -3β, and -3γ were a generous gift from R. Costa (University of Illinois) and the HES-1 antiserum was a generous gift from Y. Jan (University of California San Francisco). The anti-HNF-1α antiserum was purchased from Santa Cruz Biotechnology, Inc.

The following oligonucleotides were used as labeled probes or competitors in EMSA reactions (top strands shown):

| | | |
|---|---|---|
| H3-1: | GATCTCTCGAGAGAGCAAACAGCGCGGCGG | (SEQ ID NO:10) |
| H3-2: | TTATTATTATTTTAGCAAACACTGGAGACAG | (SEQ ID NO:11) |
| H1: | ATCTCTTGTAATTATTTATTAAACGAAATCTATT | (SEQ ID NO:12) |
| H2: | TTAAACGAAATCTATTTATTATTATTTTAGCAAA | (SEQ ID NO:13) |
| H1P: | GATCTCGCCACGAGCCACAAGGATTG | (SEQ ID NO:14) |
| E1: | GATCTAAATTTCCCCATGTGTAACGTGCAG | (SEQ ID NO:15) |
| N1: | GATCTGGAGCGGGCTCGCGTGGCGCGGCCCCG | (SEQ ID NO:16) |
| N2: | GATCTGCCGGGCAGGCACGCTCCTGGCCCGG | (SEQ ID NO:17) |
| N3/4: | GATCTAAAGCGTGCCAAGGGGCACACGACTG | (SEQ ID NO:18) |

Mapping the Human ngn3 Promoter

Figure 11A:
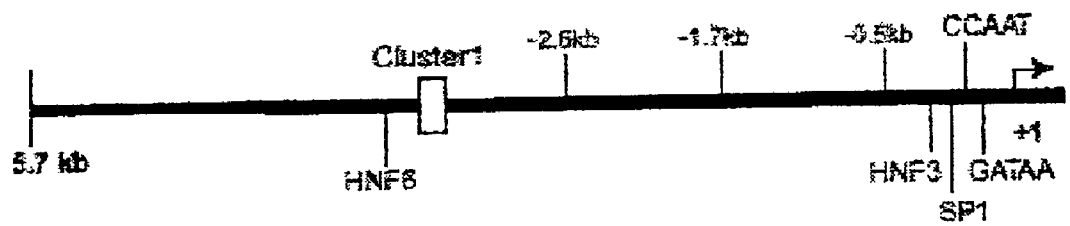
FIGS. 11A–11B is a schematic showing the human neurogenin 3 gene promoter.
Figure 11B:
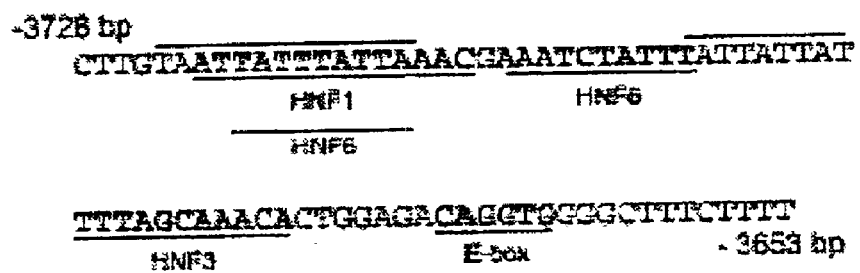

As an initial step in understanding the regulation of neurogenin3 gene expression, the sequences mouse and human neurogenin3 promoters (FIGS. 11A–11B). Using RNA purified from embryonic day 15.5 fetal mouse pancreas, the transcription start sites of the murine ngn3 gene was determined by 5' Rapid Amplification of cDNA Ends (5' RACE). All 5' RACE products identify the same start site, 30 base pairs downstream from a putative TATAA box (FIG. 11B). The region upstream of the start site is highly conserved in mouse, human and rat, with the region of highest homology in mouse and human extending approximately 300 bp upstream. A CCAAT sequence element lies at −85 bp relative to the transcription start site. Several other potential sequence elements are identified in FIG. 11B.

Activity of the Promoter in Cell Lines

Figure 12:
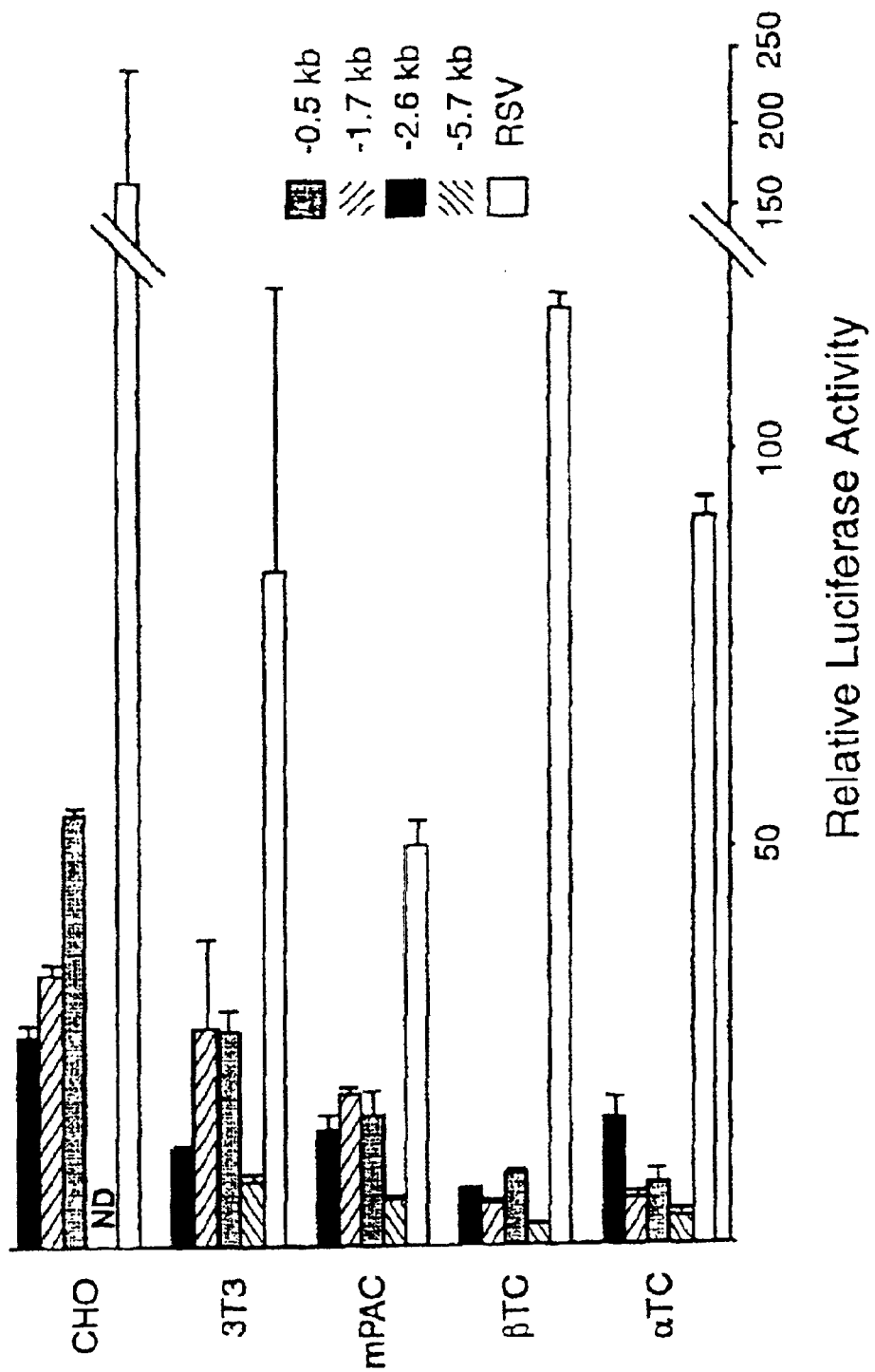
FIG. 12 is a graph showing the function of the human neurogenin 3 promoter in cell lines. Promoter fragments containing sequences extending from the 5' end indicated to +261 bp were ligated upstream of the firefly luciferase gene and transfected into the cell lines shown. Reporter gene activity is expressed relative to the promoterless luciferase vector in the same cell type. Transfections were performed in triplicate on at least two occasions and errors are shown as +/− the standard error of the mean. ND, not done.

A series of progressive 5'deletions of the neurogenin3 promoter each extending to +261 bp on the 3' end were linked to the firefly luciferase gene and were tested in cell lines (FIG. 12). Serial deletions down to −502 bp do not diminish the promoter activity in vitro. Surprisingly, the promoter drives transcription at a high level in all the tested cell lines, including the fibroblast cell lines. This high non-specific activity appears to reside in the proximal promoter, since the shortest construct is still very active in all the examined cell lines.

Activity of the Promoter in Transgenic Mice

While transient transfections in cell lines may provide some indication of promoter activity, these tumor cells are not representative of the cells in the developing pancreas where neurogenin3 is normally expressed. Therefore, mice were produced carrying a transgene with either 5.7 kb or 2.6 kb of the upstream sequence from the human neurogenin3 gene driving the bacterial gene encoding β-galactosidase. Founder mice were harvested at embryonic day 15.5, at the normal peak of neurogenin3 expression in the fetal mouse pancreas (Schwitzgebel et al. *Development* 127:3533–3542, 2000).

Figure 13A:
FIGS. 13A–13C are photographs showing the function of the human neurogenin 3 promoter in vivo.
Figures 13B, 13C:
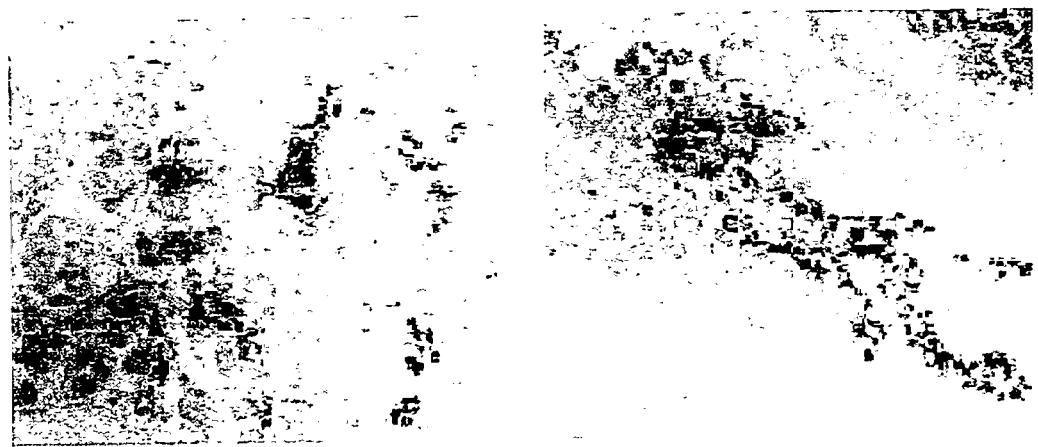

Animals carrying the 5.7 kb construct strongly and selectively express β-galactosidase in central regions of the developing pancreas and in the gut epithelium, the same regions where neurogenin3 is normally expressed at this time during development (FIG. 13A). Although the level of expression is significantly lower with the 2.6 kb construct, the overall pattern of β-galactosidase expression is the same (FIGS. 13B, 13C and data not shown).

Figure 14A:
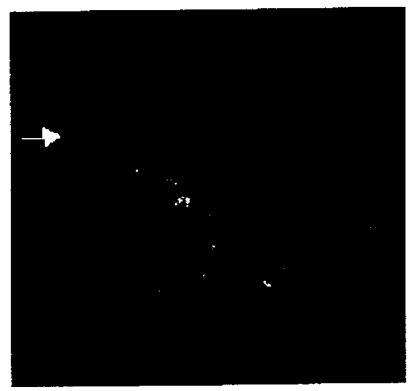
FIGS. 14A–14B are photographs showing representative cells expressing the transgene.
Figure 14B:

Immunohistochemistry was used to identify the cells expressing β-galactosidase in the transgenic mice carrying the 5.7 kb promoter construct (FIGS. 14A and 14B). The β-galactosidase expressing cells are predominantly localized to the ducts. Most of the β-galactosidase expressing cells do not express islet hormones, although occasional β-cells co-express insulin and β-galactosidase.

Despite the close co-localization of β-galactosidase activity and neurogenin3 protein expression specifically in the same regions of the developing pancreas and gut, there is not a perfect match. Some of the β-galactosidase positive cells co-express high levels of neurogenin 3, but many do not, and many neurogenin 3-expressing cells contain little or no β-galactosidase activity. Most likely this discrepancy derives from differences in the timing of accumulation and degradation of the two gene products, rather than a difference in the onset and extinction of gene expression.

The exact timing for initial detection of each gene product in a particular cell depends on its rate of accumulation and threshold for detection, and therefore should not be expected to be identical. In addition, some neurogenin3 expressing cells may randomly silence the transgene, a poorly understood phenomenon observed with many promoters in transgenic mice (Graubert et al. *Nucleic Acids Res* 26:2849–58, 1998). The very brief but abundant expression of neurogenin 3 in progenitor cells indicates that the mRNA and protein accumulate rapid1 y but have very short half-lives. β-galactosidase in contrast has a fairly long half-life in mammalian cells (Smith et al. *J. Virol* 69:4593–9, 1995) and could be expected to peak later and persist in cells after neurogenin 3 is no longer detectable. Therefore many of the β-galactosidase expressing cells apparently represent a stage of islet cell differentiation that occurs after neurogenin 3 gene production has ceased, but before hormone expression has started. The large number of these cells suggests that this intermediate stage of differentiation may last longer than the initial neurogenin 3 expressing stage.

Intestinal Expression

Figure 15A:
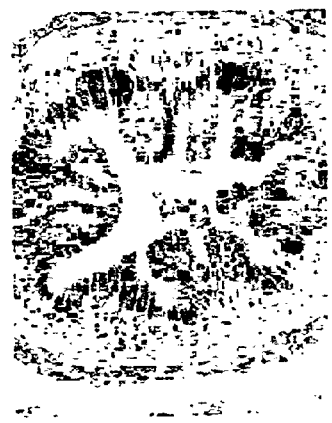
FIGS. 15A–15C are photographs showing gut expression of neurogenin 3.
Figure 15B:
Figure 15C:
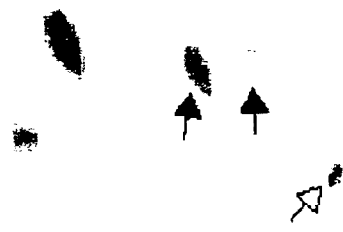

Starting at E15.5, endogenous β-galactosidase expression can be detected at low levels along the brush border of the intestinal villi in both transgenic and non-transgenic embryos. Stronger β-galactosidase activity can also be detected in a speckled pattern that is most prominent in the small intestine of the transgenic mice but is absent in their non-transgenic littermates (FIG. 13A). Sectioning of the gut reveals that this β-galactosidase signal derives from scattered cells within the intestinal epithelium (FIGS. 15A–15C). This pattern of β-galactosidase expression suggests that the neurogenin 3 promoter is also active in a subset of progenitor cells in the developing gut. These may be progenitors for gut endocrine cells. As in the pancreas, this β-galactosidase activity partially overlaps endogenous neurogenin 3 expression, again suggesting that the peak of β-galactosidase accumulation is delayed relative to neurogenin 3 (FIG. 15C).

Multiple Factors Bind to the Neurogenin3 Promoter

To identify nuclear factors that bind to the ngn3 promoter, a series of oligonucleotides were synthesized. The oligonucleotides, which spanned potentially important DNA binding sites within the promoter, were tested for binding to nuclear proteins by electromobility shift assay (EMSA).

Figure 16A:
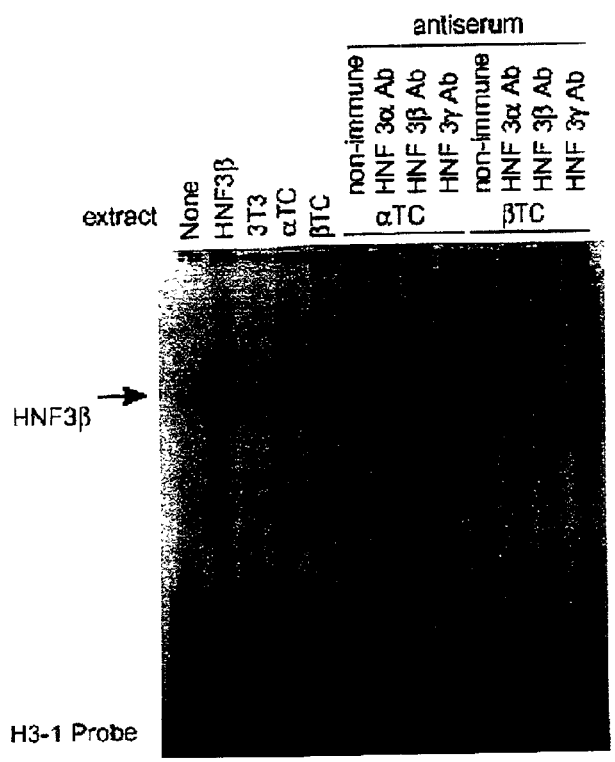
FIGS. 16A–16B are photographs of electromobility shift assays illustrating HNF3 binding to the human ngn3 promoter.
Figure 16B:
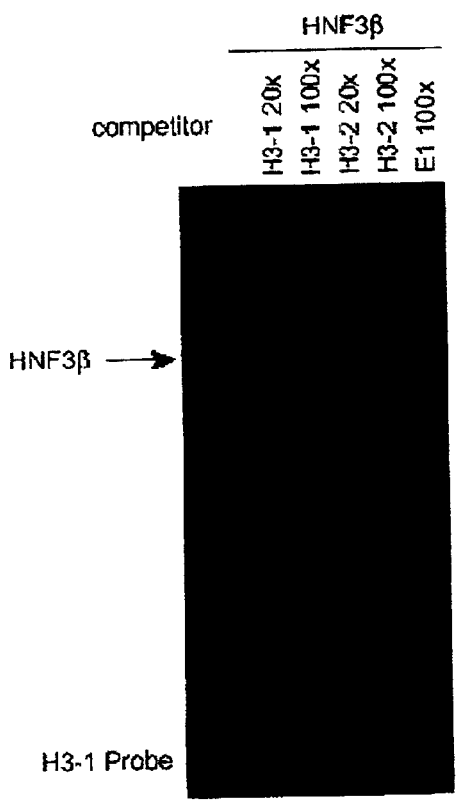

Members of the HNF3 family of winged helix transcription factors have been implicated in pancreatic development and islet function (Wu et al. *Mol Cell Biol* 17:6002–13, 1997; Gerrish et al. *J. Biol Chem* 275:3485–92, 2000; Sharma et al. *Mol Cell Biol* 17:2598–604, 1997; Duncan et al. *Science* 281:692–5, 1998; Philippe et al. *Mol Cell Biol* 14:3514–23, 1994; Kaestner et al *Genes Dev* 13:495–504, 1999). Based on their similarity to a consensus HNF3 binding site (Costa et al. *Mol Cell Biol* 9:1415–25, 1989), there are several potential HNF3 binding sites within the 5.7 kb human neurogenin3 promoter. Two of the most promising sites lie at −3687 bp and at −200 bp. EMSA testing of these binding sites showed that both sites bind with high affinity to in vitro produced HNF3β (FIG. 16). Using extracts from βTC3 and αTC1.6 cells, a single major complex binds to both sites, and is recognized specifically by an antiserum to HNF3β. In addition, co-expression of HNF3 β can activate the neurogenin3 promoter in transiently transfected 3T3 fibroblast cells (data not shown).

The −3687 bp HNF3β binding site forms part of a cluster of potential DNA binding sites for known pancreatic transcription factors (FIG. 11), including potential sites for hox type homeodomain transcription factors, as well as cut-homeodomain transcription factor HNF6 and the Pou-homeodomain HNF1 factors (Courtois et al. *Science* 238:688–92, 1987). HNF6 binding to the neurogenin3 promoter has been demonstrated previously (Jacquemin et al. *Mol Cell Biol* 20:4445–54, 2000).

Figure 17:
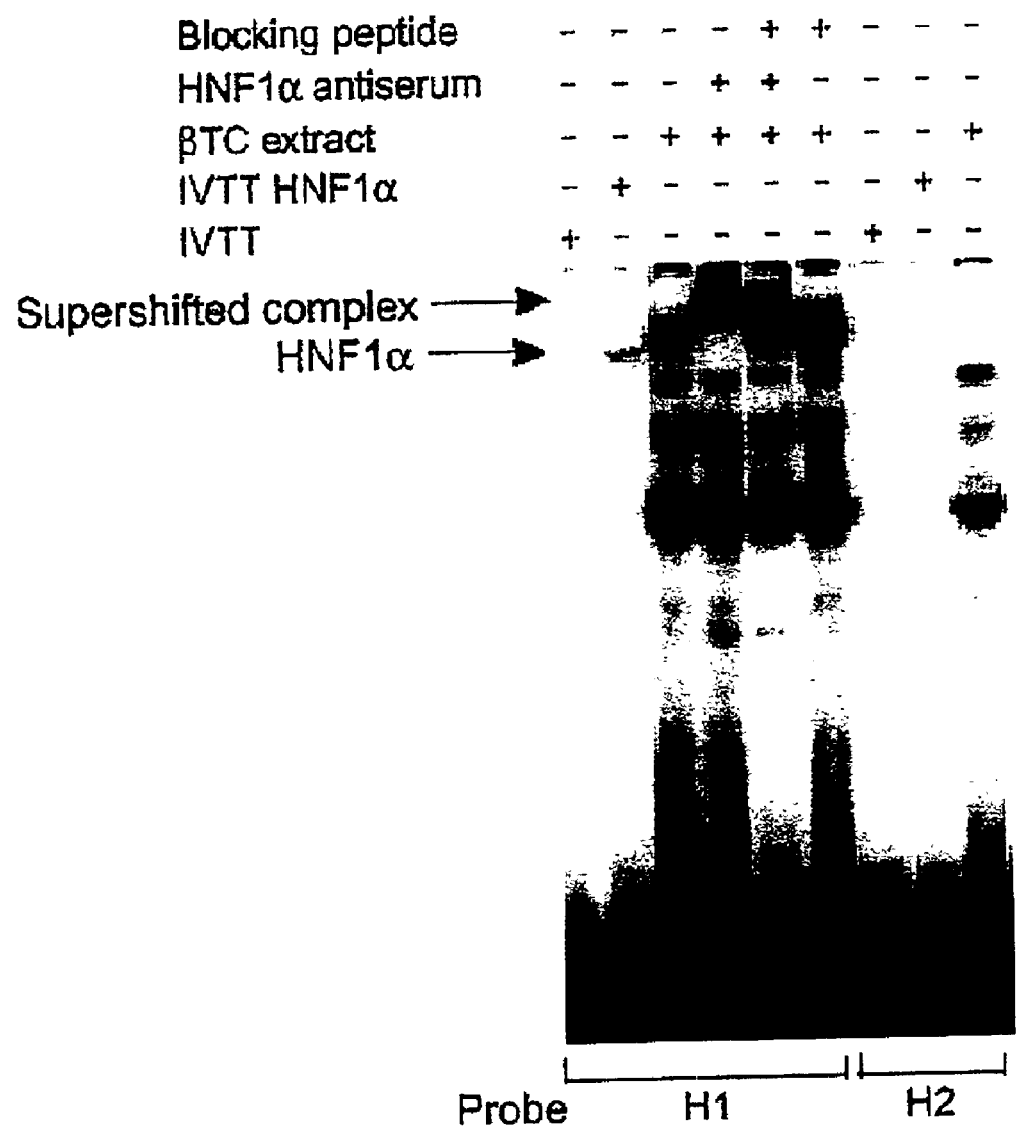
FIG. 17 is a photograph of a electromobility shift assays showing that HNF1 binds to the human ngn3 promoter.

An oligonucleotide spanning the potential HNF1 binding site was tested by EMSA and found that it can bind to in vitro produced HNF-1α. In addition, in nuclear extracts from βTC3 cells, a major low mobility complex binds to the oligonucleotide and is recognized specifically by antiserum to HNF1α (FIG. 17). The similar hox homeodomain-type binding site immediately downstream of the HNF1α binding site will not bind HNF1α (data not shown).

HES-1 Inhibition of the Neurogenin3 Promoter

It has been proposed that Notch receptor signaling through the transcriptional regulator HES-1 may prevent the expression of neurogenin3 in all but a small subset of the cells in the developing pancreas (Jensen et al. *Nat Genet* 24:36–44, 2000). To test the ability of HES-1 to directly inhibit the neurogenin3 promoter, the HES-1 cDNA was expressed from a CMV promoter-driven expression plasmid in 3T3 cells along with the neurogenin3 promoter luciferase plasmid (FIGS. 18A–18C). HES-1 dramatically and specifically inhibits the neurogenin3 promoter. Removal of 5' sequences down to −502 bp does not significantly reduce the ability of HES-1 to inhibit the promoter.

To further map sequences competent to respond to HES-1 repression, plasmids were constructed with either the human ngn3 gene promoter sequence from −208 bp to +40 bp (proximal promoter (FIG. 19A)) linked to the firefly luciferase gene, or the sequences from −2.6 kb to −208 bp (distal promoter) upstream of the herpes virus Thymidine Kinase (TK) promoter linked to the firefly luciferase gene. The small proximal promoter retains most of the capacity for HES-1 repression, while the distal sequences are repressed weakly by HES-1.

Within the proximal 208 bp of the promoter, there are several potential HES-1 binding sites based on the consensus binding sites for HES-1 (CTNGTG) (Takebayashi et al. *J. Biol Chem* 269:5150–6, 1994) and its *Drosophila* homologs hairy/enhancer-of-split (CGCGTC) (Van Doren et al. *Genes Dev* 8:2729–42, 1994; Ohsako et al. *Genes Dev* 8:2743–55, 1994) (FIG. 19A). Three oligonucleotides containing four of these sites were tested for binding to bacterially produced HES-1 protein by gel mobility shift assay (FIG. 19B). All three oligonucleotides bind HES-1, and do so with greater affinity than the previously described high affinity tandem sites from the mouse HES-1 gene (Takebayashi et al. *J. Biol Chem* 269:5150–6, 1994) (labeled H1 in FIG. 19C). All four of these sequences are conserved in the mouse neurogenin3 promoter (FIG. 11).

The invention now being fully described, it will be apparent to one of ordinary skill in the art that many changes and modifications can be made thereto without departing from the spirit or scope of the appended claims.

What is claimed is:

1. A method for producing an insulin-producing cell in vitro, the method comprising:
    introducing a nucleic acid molecule operably linked to a promoter into a cell in vitro, the nucleic acid molecule encoding a neuroendocrine class B basic helix-loop-helix (bHLH) transcription factor, said introducing being in an amount sufficient for production of the neuroendocrine bHLH transcription factor and production of an insulin-producing cell;

wherein said cell is a cultured gastrointestinal organ cell.

2. The method of claim 1, wherein the neuroendocrine bHLH transcription factor is neurogenin3.

3. The method of claim 1, wherein the neuroendocrine bHLH transcription factor is neurogenin1, neurogenin2, NeuroD1BETA2, neuroD2, math2, NeuroD4/Math3, math1/ATOH1, mash1/ASCL1/ASH1 or mash2.

4. The method of claim 1, wherein the insulin-producing cell produced is an insulin-producing islet cell.

5. A method for producing a mammalian insulin-producing cell in vitro, the method comprising the steps of:
introducing into a mammalian cell in vitro a nucleic acid molecule operably linked to a promoter, the nucleic acid molecule encoding a neuroendocrine class B bHLH transcription factor, wherein said introducing provides for expression of the transcription factor in the mammalian cell and production of insulin in the mammalian cell;
wherein said mammalian cell is a cultured gastrointestinal organ cell.

6. The method of claim 5, wherein the mammalian cell is a pancreatic cell.

7. The method of claim 5, wherein the neuroendocrine bHLH transcription factor is neurogenin3.

8. The method of claim 5, wherein the neuroendocrine bHLH transcription factor is neurogenin1, neurogenin2, NeuroD1/BETA2, neuroD2, math2, NeuroD4/Math3, math1/ATOH1, mash1/ASCL1/ASH1 or mash2.

9. A method for producing a mammalian insulin-producing cell in vitro, the method comprising the steps of:
introducing into a mammalian pancreatic cell in vitro a nucleic acid molecule the nucleic acid molecule being operably linked to a promoter, said nucleic acid molecule encoding neurogenin3 (Ngn3), wherein said introducing provides for expression of Ngn3 in the cell and production of insulin in the cell.

10. A method for delivering insulin to the bloodstream of a mammalian subject, the method comprising:
introducing an insulin-producing cell produced by the method of claim 9 into a mammalian subject, wherein said introducing provides for production of insulin by the insulin-producing cell and delivery of insulin to the bloodstream of the mammalian subject.

11. A method for delivering insulin to the bloodstream of a mammalian subject, the method comprising:
introducing an insulin-producing cell produced by the method of claim 1 into a mammalian subject, wherein said introducing provides for production of insulin by the insulin-producing cell and delivery of insulin to the bloodstream of the mammalian subject.

12. A method for delivering insulin to the bloodstream of a mammalian subject, the method comprising:
introducing an insulin-producing cell produced by the method of claim 5 into a pancreas of a mammalian subject, wherein said introducing provides for production of insulin by the insulin-producing cell and delivery of insulin to the bloodstream of the mammalian subject.

13. The method of claim 1, where the cultured gastrointestinal organ cell is a cultured adult pancreatic cell.

14. The method of claim 1, wherein said cultured gastrointestinal organ cell is a pancreas cell.

15. The method of claim 1, wherein said cultured gastrointestinal organ cell is a liver cell.

16. The method of claim 5, wherein said cultured gastrointestinal organ cell is a liver cell.

17. A method for producing insulin in vitro, comprising:
culturing a gastrointestinal organ cell in vitro to produce insulin, wherein said cell comprises a recombinant nucleic acid molecule comprising a nucleic acid molecule encoding a neuroendocrine class B basic helix-loop-helix (bHLH) transcription factor operably linked to a promoter.

18. The method of claim 17, wherein the neuroendocrine bHLH transcription factor is neurogenin1, neurogenin2, NeuroD1/BETA2, neuroD2, math2, NeuroD4/Math3, math1/ATOH1, mash1/ASCL1/ASH1 or mash2.

19. The method of claim 17, wherein said gastrointestinal organ cell is a pancreatic or liver cell.

20. The method of claim 17, wherein said gastrointestinal organ cell is a gut or salivary gland cell.

21. The method of claim 1, wherein said cultured gastrointestinal organ cell is a cultured gut or salivary gland cell.

* * * * *